United States Patent [19]

Heintz et al.

[11] Patent Number: 5,217,864
[45] Date of Patent: Jun. 8, 1993

[54] REPLICATION INITIATOR PROTEIN COMPLEX AND METHODS OF USE THEREOF

[75] Inventors: Nathaniel Heintz, Pelham Manor; Lisa A. Dailey, New York, both of N.Y.; Nicholas H. Heintz, Jericho, Vt.; Mark S. Caddle, Woodside, Calif.

[73] Assignees: The Rockefeller University, New York, N.Y.; University of Vermont, Burlington, Vt.

[21] Appl. No.: 573,570

[22] Filed: Aug. 27, 1990

[51] Int. Cl.⁵ .................................. C12Q 1/68
[52] U.S. Cl. ............................. 435/6; 435/7.8; 435/68.1; 435/70.1; 935/36
[58] Field of Search .............. 435/6, 68.1, 70.1; 455/7.8; 935/36

[56] References Cited

U.S. PATENT DOCUMENTS 4,792,520 12/1988 Stambrook et al. ............... 435/6

OTHER PUBLICATIONS

Wun-Kim et al., "Mapping of Helicase and Helicase Substrate-Binding Domains on Simian Virus 40 Large T Antigen," J. Virology, 64 pp. 2014-2030 (1990).
Anachkova et al., Mol. Cell. Biol., 9, pp. 532-540 (1989), "Replication of the Amplified Dihydrofolate Reductase Domain in CHO Cells May Initiate at Two Distinct Sites, One of Which is a Repetitive Sequence Element."
Anderson, Nucleic Acids Res., 14, pp. 8513-8533 (1986), "Detection, Sequence Patterns, and Functions of Unusual DNA Structures."
Angel et al., Cell, 49, pp. 729-739 (1987), "Phorbol Ester-Inducible Genes Contain a Common Cis Element Recognized by a TPA-Modulated Trans-Acting Factor."
Baker et al., J. Biol. Chem., 262, pp. 6877-6885 (1987), "Helicase Action of dnaB Protein During Replication from the Escherichia coli Chromosomal Origin in Vitro."
Baker et al., Cell, 55, pp. 113-123 (1988), "Transcriptional Activation of the Initiation of Replication from the E. coli Chromosomal Origin: An RNA-DNA Hybrid Near oriC."
Bramhill et al., Cell, 52, pp. 743-745 (1988), "Duplex Opening by dnaA protein at Novel Sequences in Initiation of Replication at the Origin of the E. coli Chromosome."
Bramhill et al., Cell, 54, pp. 915-918 (1988), "A Model for Initiation at Origins of DNA Replication."
Buchman et al., Mol. Cell. Biol., 8, pp. 210-225 (1988), "Two DNA-Binding Factors Recognize Specific Sequences at Silencers, Upstream Activating Sequences, Autonomously Replicating Sequences and Telomeres in Saccharomyces cerevisiae."
Burhans et al., Proc. Natl. Acad. Sci. USA, 83, pp. 7790-7794 (1986), "Isolation of the Origin of Replication Associated with the Amplified Chinese Hamster Dihydrofolate Reductase Domain."
Burhans et al., Cell, 62, pp. 955-965 (1990), "Identification of an Origin of Bidirectional DNA Replication in Mammalian Chromosomes."

(List continued on next page.)

Primary Examiner—Esther L. Kepplinger
Assistant Examiner—Donna C. Wortman
Attorney, Agent, or Firm—Klauber & Jackson

[57] ABSTRACT

A replication initiator protein complex for eukaryotic cells is disclosed which includes protein fractions of about 60 kD and 100 kD size. The protein complex comprises a protein in purified form that is capable of origin-specific DNA binding and ATP-dependent DNA helicase activity. The 60 kD fraction is named RIP60 and is primarily active in origin-specific DNA binding. The 100 kD fraction is named RIP100 and is primarily active as a DNA helicase. The protein complex and its fractions are active only during S phase and thereby commend their investigation and use toward the development of specific diagnostic and therapeutic modalities against pathogens to which cell division is critical. Diagnostic and therapeutic utilities are accordingly proposed, and testing procedures, materials in kit form, recombinant materials and procedures, and pharmaceutical compositions are likewise set forth.

3 Claims, 9 Drawing Sheets

OTHER PUBLICATIONS

Caddle et al., *Mol. Cell. Biol.*, 10, pp. 6236–6243 (1990), "RIP60, A Mammalian Origin-Binding Protein, Enhances DNA Bending Near the Dihydrofolate Reductase Origin of Replication."

Caddle et al., *J. Mol. Biol.*, 211, pp. 19–33 (1990), "Intramolecular DNA Triplexes, Bent DNA, and DNA Unwinding Elements in the Initiation Region of a Amplified Dihydrofolate Reductase Replicon."

Celniker et al., *Mol. Cell Biol.*, 4, pp. 2455–2466 (1984), "Deletion Mutations Affecting Autonomously Replicating Sequence ARS1 of *Saccharomyces cerevisiae*."

Chodosh et al., *Mol. Cell. Biol.*, 6, pp. 4723–4733 (1986), "A Single Polypeptide Possesses the Binding and Transcription Activities of the Adenovirus Major Late Transcription Factor."

Dailey et al., *Genes Dev.*, 2, pp. 1700–1712 (1988), "Purification of the Human Histone H4 Gene-Specific Transcription Factors H4TF-1 and H4TF-2."

Dean et al., *Proc. Natl. Acad. Sci. USA*, 84, pp. 16–20 (1987), "Simian Virus 40 (SV40) DNA Replication: SV40 Large T Antigen Unwinds DNA Containing the SV40 Origin of Replication."

Deb et al., *Mol. Cell. Biol.*, 6, pp. 5478–4584 (1986), "The Adenine-Thymine Domain of the Simian Virus 40 Core Origin Directs DNA Bending and Coordinately Regulates DNA Replication."

DePamphillis, *Cell*, 52, pp. 635–538 (1988), "Transcriptional Elements as Components of Eukaryotic Origins of DNA Replication."

Digman et al., *Methods Enzymol.*, 101, pp. 582–598 (1983), "Eukaryotic Gene Transcription with Purified Components."

Eckdahl et al., *Nucleic Acids Res.*, 18, pp. 1609–1612 (1990), "Conserved DNA Structures in Origins of Replication."

Fried et al., *Nucleic Acids Res.*, 9, pp. 6505–6525 (1981), "Equilibria and Kinetics of Lac Repressor-Operator Interactions by Polyacrylamide Gel Electrophoresis."

Galas et al., *Nucleic Acids Res.*, 5, pp. 3157–3170 (1978), "DNase Footprinting: A Simple Method for the Detection of Protein-DNA Binding Specificity."

Garner et al., *Nucleic Acids Res.*, 9, pp. 3047–3060 (1981), "A Gel Electrophoresis Method for Quantifying the Binding Proteins to Specific DNA Regions: Application to Components of the *Escherichia coli* Factors Operon Regulatory System."

Handeli et al., *Cell*, 57, pp. 909–920 (1989), "Mapping Replication Units in Animal Cells."

Heintz et al., *Proc. Natl. Acad. Sci. USA*, 79, pp. 4083–4087 (1982), "An Amplified Chromosomal Sequence that Includes the Gene for Dihydrofolate Reductase Initiates Replication Within Specific Restriction Fragments."

Heintz et al., *Nature* (London), 302, pp. 439–441 (1983), "Cloning of the Initiation Region of a Mammalian Chromosomal Replicon."

Heintz et al., *Mol. Cell. Biol.*, 8, 1923–1931 (1988), "Nuclear DNA Synthesis In Vitro is Mediated Via Stable Replication Forks Assembled in a Temporally Specific Fashion In Vivo."

Holmes et al., *Mol. Cell. Biol.*, 9, pp. 5464–5472 (1989), "Interaction of the H4 Autonomously Replicating Sequence Core Consensus Sequence and Its 3′-Flanking Domain."

Kearsey, *Cell*, 37, pp. 299–307 (1984), "Structural Requirements for the Function of a Yeast Chromosomal Replicator."

Kipling et al., *Mol. Cell. Biol.*, 10, pp. 265–272 (1990), "Reversion of Autonomously Replicating Sequence Mutations in *Saccharomyces cerevisiae*: Creation of a Eucaryotic Replication Origin Within Procaryotic Vector DNA."

Kowalski, *Nucleic Acids Res.*, 12, pp. 7071–7086 (1984), "Changes in Site Specificity of Single-Strand-Specific Endonucleases on Supercoiled PM2 DNA with Temperature and Ionic Environment."

Kowalski et al., *EMBO J.*, 8, pp. 4335–4344 (1989), "The DNA Unwinding Element: A Novel, Cis-Acting Component that Facilitates Opening of the *Escherichia coli* Replication Origin."

LaBella, *Genes & Develop.*, 3, pp. 1981–1990 (1989), "Histone H1 Subtype-Specific Consensus Elements Mediate Cell Cycle-Regulated Transcription In Vitro."

Lahue et al., *J. Biol. Chem.*, 263, pp. 3208–3215 (1988), "*Escherichia coli* DNA Helicase I Catalyzes a Unidirectional and Highly Processive Unwinding Reaction."

Laundon et al., *Cell*, 52, pp. 545–549 (1988), "Curved

Helix Segments Can Uniquely Orient the Topology of Supertwisted DNA."

Leu et al., *Mol. Cell. Biol.*, 9, pp. 523–531 (1989), "High-Resolution Mapping of Replication Fork Movement Through the Amplified Dihydrofolate Reductase Domain in CHO Cells by In-Gel Renaturation Analysis."

Maxam et al., *Methods Enzymol*, 65, pp. 499–560 (1980), "Sequencing End-Labeled DNA With Base-Specific Chemical Cleavages."

Milbrandt et al., *Proc. Natl. Acad. Sci. USA*, 78, pp. 6043–6047 (1981), "Methotrexate-Resistant Chinese Hamster Ovary Cells Have Amplified a 135-Kilobase-Pair Region That Includes the Dihydrofolate Reductase Gene."

Mukherjee et al., *Proc. Natl. Acad. Sci. USA*, 85, pp. 6287–6291 (1988), "Detection of DNA Looping Due to Simultaneous Interaction of a DNA-Binding Protein with Two Spatially Separated Binding Sites on DNA."

Olivo et al., *Proc. Natl. Acad. Sci. USA*, 85, pp. 5414–5418 (1988), "Herpes Simplex Virus DNA Replication: The UL9 Gene Encodes an Origin-Binding Protein."

O'Neill et al., *Science*, 241, pp. 1210–1213 (1988), "Transcription Factor OTF-1 is Functionally Identical to the DNA Replication Factor NF-III."

Prives et al., *Mol. Cell. Biol.*, 5, pp. 3694–3704 (1987), "DNA Sequence Requirements for Replication of Polyomavirus DNA In Vivo and In Vitro."

Ramstein et al., *Proc. Natl. Acad. Sci. USA*, 85, pp. 7231–7235 (1988); "Energetic Coupling Between DNA Bending and Base Pair Opening."

Reisman et al., *Mol. Cell. Biol.*, 5, pp. 1822–1832 (1985), "A Putative Origin of Replication of Plasmids Derived from Epstein-Barr Virus is Composed to Two cis-acting Components."

Rosenfeld et al., *J. Biol. Chem.*, 261, pp. 1398–1408 (1986), "Purification of Nuclear Factor I by DNA Recognition Site Affinity Chromatography."

Schnos et al., *Cell*, 52, pp. 385–395 (1988), "Initiation Protein Induced Helix Destabilization at the Lambda Origin: A Prepriming Step in DNA Replication."

Snyder et al., *Nature* (London), 324, pp. 87–89 (1986), "Bent DNA at a Yeast Autonomously Replicating Sequence."

Solomon et al., *Proc. Natl. Acad. Sci. USA*, 83, pp. 1276–1280 (1986), "A Mammalian High Mobility Group Protein Recognizes any Stretch of Six A-T Base Pairs in Duplex DNA."

Sopta et al., *Nature* (London), 341, pp. 410–414 (1989), "Structure and Associated DNA-Helicase Activity of a General Transcription Initiation Factor that Binds to RND Polymerase II."

Stahl et al., *EMBO J.*, 5, pp. 1939–1944 (1986), "DNA Helicase Activity of SV40 Large Tumor Antigen."

Umek et al., *Nucleic Acids Res.*, 15, pp. 4467–4480 (1987), "Yeast Regulatory Sequences Preferentially Adopt a Non-B Conformation in Supercoiled DNA."

Umek et al., *Cell*, 52, pp. 559–567 (1988), "The Ease of DNA Unwinding as a Determinant of Initiation at Yeast Replication Origins."

Unek et al., *Biochim. Biophys. Acta*, 1007, pp. 1–14 (1989), "New Beginnings in Studies of Eukaryotic DNA Replication Origins."

Veldman et al., *Mol. Cell. Biol.*, 5, pp. 649–658 (1985), "Polyomavirus Enhancer Contains Multiple Redundant Sequence Elements that Activate Both DNA Replication and Gene Expression."

Williams et al., *Mol. Cell. Biol.*, 8, pp. 2763–2769 (1988), "Bent DNA Functions as a Replication Enhancer in *Saccharomyces cerevisiae*."

Wu et al., *Science*, 238, pp. 1247–1253 (1987), "Purification and Properties of Drosophila Heat Shock Activator Protein."

Zahn et al., *Nature* (London), 317, pp. 451–453 (1985), "Sequence-Induced DNA Curvature at the Bacteriophage Lambda Origin of Replication."

Zahn et al., *Science*, 236, pp. 416–422 (1987), "Direct Evidence for DNA Bending at the Lambda Replication Origin."

Zweib et al., *Genes Dev.*, 3, pp. 606–611 (1989), "DNA Bending by Negative Regulatory Proteins: Gal and Lac Repressors."

```
                                          RIP60
                          ┌─────────────────────────────┐
5'-AAAATGACTCAAAACTAGTTTTTTTATTATTATTATTAGTTC-3'
3'-TTTTACTGAGTTTTGATCAAAAAAATAATAATAATAATCAAG-5'
                          └─────────────────────────────┘
  ▭▭          ▭▭        ▭▭
  B3          B4        B5
```

FIG. 9A SDS-PAGE
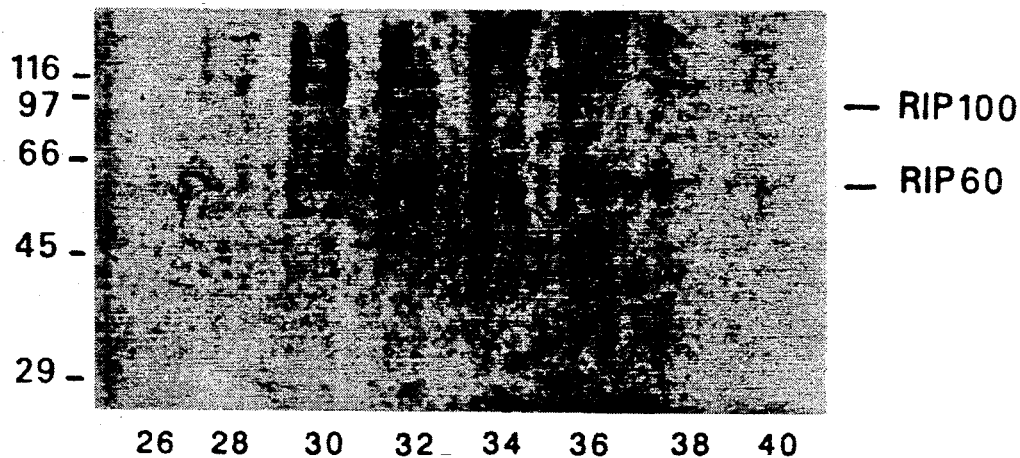
FIG. 9B Specific DNA Binding
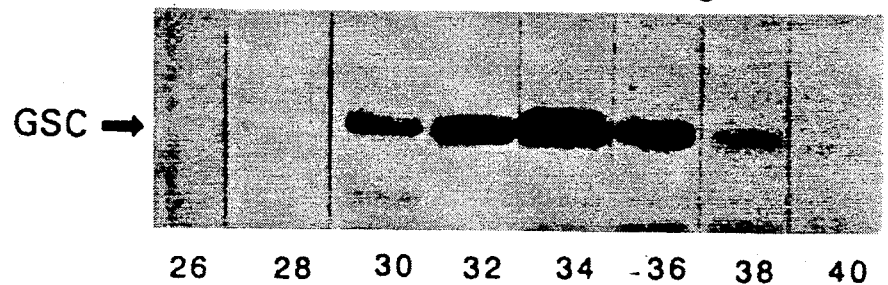
FIG. 9C DNA Helicase Activity
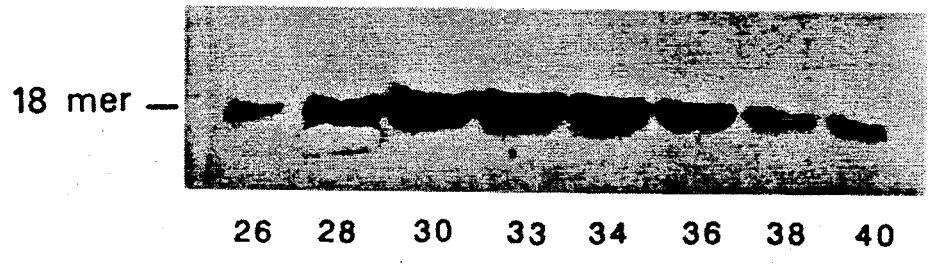
FIG. 9D Labeling with ATP
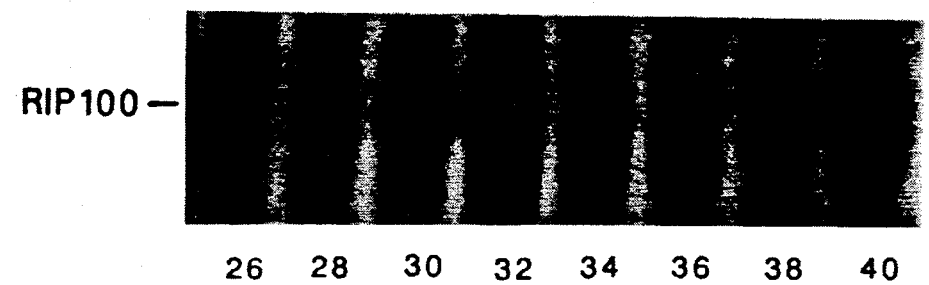

REPLICATION INITIATOR PROTEIN COMPLEX AND METHODS OF USE THEREOF

RELATED PUBLICATIONS

The Applicants are authors or co-authors of several articles directed to the subject matter of the present invention. (1) [Applicant Nathaniel Heintz co-authored with F. LaBella, P. Galinari and J. McKinney] "Histone H1 Subtype Specific Consensus Elements Mediate Cell Cycle-regulated Transcription in vitro" GENES AND DEVELOPMENT 3:1982-1990 (1989); and (2) [All Applicants co-authored] "Purification of RIP60 and RIP100, Mammalian Proteins with Origin-Specific DNA Binding and ATP-Dependent DNA Helicase Activities" *Molecular and Cellular Biology*, vol. 10, pp. 6225-6235, December 1990. Both of the above listed articles are incorporated herein by reference.

The research leading to the present invention was funded in part by grants from the National Institutes of Health and the Howard Hughes Medical Institute. The Government may have certain rights in this invention.

BACKGROUND OF THE INVENTION

The present invention relates to a newly discovered and purified protein complex and to methods and compositions including such protein complex in assays and for diagnosing, preventing and/or treating cellular debilitation, derangement or dysfunction. More particularly, the present invention relates to a molecule or molecules that specifically promote S phase activity, and to antibodies or to other entities specific thereto that may thereby selectively inhibit S phase activity of mammalian cells.

The study of DNA replication in a variety of prokaryotic chromosomes, bacteriophages, and eukaryotic viruses has facilitated the construction of a general model for initiation of DNA synthesis at origins of replication (Bramhill, D., & Kornberg, A. (1988). CELL, 54, 915-918). In the general model, initiation is viewed a stepwise process that involves the ordered interaction of multiple proteins with origin DNA sequences. Origin activation commences with the binding of a replication initiator protein to origin-specific recognition sequences, which are often reiterated. Binding of the initiator protein engenders DNA melting at the origin, leading to the formation of a stable presynthesis complex that contains locally unwound DNA (Bramhill & Kornberg, 1988; Dean, F. B. et al. (1987). PROC. NATL. ACAD. SCI. USA, 84, 16-20; Schnos, M. et al. (1988). CELL, 52, 385-395). The presynthesis complex, in turn, fosters the assembly of the multi-enzyme complexes required for bidirectional DNA replication. The timing and frequency of initiation may be regulated by the availability of the initiator protein, or by topological perturbations in the DNA template that affect the ability of the initiator protein to unwind origin sequences (Baker, T. A., & Kornberg, A. 1988). CELL, 55, 113-123). Other mechanisms of initiation of DNA synthesis may be extant in eukaryotic cells.

Like transcriptional promoters, origins of replication are complex regulatory elements with multiple modular components, including DNA unwinding elements (Umek, R. M. et al. (1989). BIOCHIMICA ET BIOPHYSICA ACTA, 1007, 1-14), binding sites for the initiator and accessory factors, and often transcriptional enhancers and promoters (DePamphillis, M. L. (1988). CELL, 52, 635-638). Despite the diversity of organization among origins of replication, unwinding at the origin is likely to be a universal prerequisite for initiation of bidirectional DNA synthesis on duplex DNA templates.

Both DNA sequences and proteins contribute to DNA unwinding at origins of replication. The DNA sequences that facilitate origin unwinding, including DNA unwinding elements, are generally AT-rich, and may have special structural properties. Another structural element, stably bent DNA, is a functional component of several known replication origins, in bacteriophages, yeasts, and papovaviruses. DNA bending may promote helix disruption, foster the functional interaction of protein binding sites, or serve to uniquely orient the topology of origins for subsequent activation of events. The relationship between those origin sequences that promote DNA bending and those that permit facile DNA unwinding is as yet unknown.

In addition to sequence determinants that promote helix instability, extensive unwinding of origin DNA requires the action of a DNA helicase. The helicase activity may be an inherent property of the initiator protein as in SV40 large T-antigen (Stahl, H. et al. (1986). EMBO. J., 5, 1939-1944) and the Herpes Simplex Virus UL-9 protein (Olivo, P. D. et al. (1988). PROC. NATL. ACAD. SCI. USA, 85, 5414-5418), or may comprise a distinct factor that interacts in a specific fashion with the initiator protein-origin DNA complex. The helicase involved in initiation may also be required at replication forks during the elongation phase of DNA synthesis, and therefore might not represent an initiation-specific replication factor.

Insight into the mechanisms that regulate initiation of DNA synthesis in higher eukaryotic cells requires knowledge of the DNA sequences that comprise chromosomal origins of replication, and purification of the cognate factors that interact with origin sequences during entry into the S phase. Although extensive genetic, biochemical and physical evidence suggests that DNA synthesis begins at preferred sites in higher eukaryotes, the lack of a satisfactory, functional assay has greatly impeded the isolation of origins of replication from animal cells, and accordingly no one has yet identified the proteins or enzymes which initiate replication of chromosomal DNA in higher eukaryotes or animal cells.

A need therefore exists to further elucidate the structure and activity of the replication initiator for animal cells, and to derive therefrom improved diagnostic techniques, and therapeutic modalities that offer the promise of greater efficacy and concomitantly reduced risk of injury to non-target cells.

SUMMARY OF THE INVENTION

In accordance with a first aspect of the present invention, a replication initiator protein complex has been discovered and purified. The replication initiator protein complex as presently isolated comprises two protein subunits, named by the applicants herein RIP60 and RIP100, respectively. The subunits appear to operate in association with each other with overlapping activities, to promote and participate in chromosomal DNA replication.

The most significant affirmative activities exhibited by the present replication initiator protein complex appears to be its specificity for chromosomal DNA replication. Accordingly, while the exact role that the present protein complex plays in the cascade of reactions leading to the S phase of the cell cycle is as yet undefined, its exclusive participation in S phase activities is clear. More particularly, the present protein complex exhibits origin-specific DNA binding activity and ATP-dependent DNA helicase activity, the former primarily attributable to RIP60 and the latter primarily attributable to RIP100.

The protein complex of the present invention is also distinctive in the activities that it lacks. In particular, the present protein complex appears to be inactive and irrelevant to the function of cells that are in the resting or $G_1$ phase, or that are simply not undergoing division. This specificity is believed to commend the present protein complex for use in diagnostic and therapeutic applications where a significant characteristic of the cells that are the targets of examination or treatment, is their entry and participation in S phase activity. Accordingly, the replication initiator protein complex possesses the potential for use, for example, as a new drug assay to identify inhibitors of S phase initiation which could serve to selectively limit the growth of undesirable cells; or as a diagnostic tool, for example, to assist in identifying the infirmity of cellular colonies that appear to be inexplicably incapable of either entering or participating in S phase.

As noted above, the present replication initiator protein complex has been identified and characterized and found to comprise two protein subunits of about 60 and 100 kilodaltons (kD) in size, respectively, by a combination of ion exchange and oligonucleotide affinity chromatography, followed by silver stained sodium dodecyl sulfate-polyacrylamide gel electrophoresis (SDS-PAGE).

The present protein complex may be prepared by the incubation of the origin of replication of a eukaryotic gene having adjacent thereto stably bent DNA with nuclear material from cells believed to be either likely to or undergoing cell division, followed by separation and purification of the desired protein complex. Thus, for example, the origin of replication of the Chinese hamster dihydrofolate reductase (dhfr) gene having adjacent thereto a fragment of stably bent DNA or domain B of the ARS1 region of yeast cells, or related DNA sequences, may be incubated with nuclear extracts of HeLa cells, and the resulting mass thereafter separated and purified by known isolation and purification techniques to recover the protein complex. The present invention naturally contemplates alternate means for preparation of the replication initiator protein complex, including where applicable known genetic replicative techniques, and the invention is accordingly intended to cover such synthetic preparations within its scope.

The isolation of the cDNA amino acid sequence will facilitate the reproduction of the replication initiator protein complex by recombinant genetic techniques as discussed in detail hereinafter. Thus, the DNA sequence encoding the present replication initiator protein complex or analogs thereof can be used to construct vectors for expression in host systems by recombinant DNA techniques.

The invention includes an assay system for screening of potential drugs effective to inhibit S phase activity of mammalian cells by counteracting the replication initiator complex may be prepared. In one instance, the test drug could be administered to a cellular sample or extract with the protein complex, to determine its effect upon the binding activity of the complex to either the sample or extract, or to the test drug, by comparison with a control. Further, the inhibitor drug, could be incubated with cells entering S phase or engaged in S phase activity to determine its effect upon cell division.

The assay system could more importantly be adapted to identify drugs or other entities that, by their capability for inhibiting S phase activity by binding to the nuclear material of such cells in a competitive fashion with the present replication initiator protein complex, could selectively attack such cells while leaving unharmed the adjacent non-dividing cellular masses. Such assay would be useful in the development of drugs that are specific against rapidly dividing cells such as neoplastic cells and viruses. For example, such drugs might be used to treat precancerous lesions, particularly of the skin and more generally, to serve as chemotherapeutic agents against neoplastic invasion.

The present invention likewise extends to the development of antibodies against the replication initiator protein complex, including naturally raised and recombinantly prepared antibodies. Such antibodies could include both polyclonal and monoclonal antibodies prepared by known genetic replicative techniques, as well as antibodies including other functionalities suiting them for additional therapeutic use conjunctive with their capability of interrupting S phase cellular activity.

The present invention also relates to a method for assessing the growth of cells by measuring the activity and presence of the replication initiator protein complex of the present invention. More particularly, the activity of the replication initiator protein complex may be followed directly by the assay techniques discussed later on, through the use of an appropriately labeled quantity of the replication initiator protein complex. Alternately, the replication initiator protein complex can be used to raise binding partners or antibodies that could in turn, be labeled and introduced into a cellular mass containing sample withdrawn from a mammalian host, to test for the presence of S phase activity, and to thereby assess the state of the host from which the medium was drawn.

Thus, both the replication initiator protein complex and any antibodies that may be raised thereto, are capable of use in connection with various diagnostic techniques, including immunoassays, such as a radioimmunoassay, using for example, an antibody to the replication initiator protein complex that has been labeled by either radioactive addition, reduction with sodium borohydride, or radioiodination.

In an immunoassay, a control quantity of the replication initiator protein complex, antibodies thereto, or the like may be prepared and labeled with an enzyme, a specific binding partner and/or a radioactive element, and may then be introduced into a cellular sample of a mammal believed to be undergoing cell division. After the labeled material or its binding partner(s) has had an opportunity to react with sites within the sample, the resulting mass may be examined by known techniques, which may vary with the nature of the label attached.

In the instance where a radioactive label, such as the isotopes $^{14}C$, $^{131}I$, $^{3}H$, $^{125}I$ and $^{35}S$ are used, known currently available counting procedures may be utilized. In the instance where the label is an enzyme, detection may be accomplished by any of the presently utilized colorimetric, spectrophotometric, fluorospectrophotometric or gasometric techniques known in the art.

The present invention includes an assay system which may be prepared in the form of a test kit for the quantitative analysis of the extent of the presence of the replication initiator protein complex. The system or test kit may comprise a labeled component prepared by one of the radioactive and/or enzymatic techniques discussed herein, coupling a label to the protein complex; and one or more additional immunochemical reagents, at least one of which is a free or immobilized ligand, capable either of binding with the labeled component, its binding partner, one of the components to be determined or their binding partner(s).

In a further embodiment, the present invention relates to certain therapeutic methods which would be based upon the activity of the replication initiator protein complex, its subunits, antibodies to the replication initiator protein complex or its subunits, or upon agents or other drugs determined to possess the same or an antagonistic activity. A first therapeutic method is associated with the prevention of the manifestations of conditions causally related to or following from the binding activity of the protein complex or its subunits, and comprises administering either an antibody to the protein complex or subunits therof, an agent capable of modulating the production and/or activity of the protein complex or subunits thereof, or an agent not an antibody to the protein complex or subunits thereof that is capable of acting as an antagonist to the protein complex or subunits thereof, either individually or in mixture with each other in an amount effective to prevent the development of those conditions in the host.

More specifically, the therapeutic method generally referred to herein could include the method for the treatment of various forms of cancer by the administration of pharmaceutical compositions that may comprise effective quantities of antibodies to the replication initiator protein complex or its subunits, or other equally effective drugs developed for instance by a drug screening assay prepared and used in ,accordance with a further aspect of the present invention.

Accordingly, it is a principal object of the present invention to provide a replication initiator protein complex and its subunits in purified form that exhibits certain characteristics and activities associated with cellular division in mammals.

It is a further object of the present invention to provide methods for the preparation of the replication initiator protein complex and its subunits, including recombinant means.

It is a further object of the present invention to provide antibodies to the replication initiator protein complex and its subunits, and methods for their preparation, including recombinant means.

It is a further object of the present invention to provide a method for detecting the presence of the replication initiator protein complex and its subunits in mammals in which invasive, spontaneous, or idiopathic pathological states such as cancer and viral infection are suspected to be present.

It is a further object of the present invention to provide a method and associated assay system for screening substances such as drugs, agents and the like, potentially effective in either mimicking the activity or combating the adverse effects of the replication initiator protein complex and/or its subunits in mammals.

It is a still further object of the present invention to provide a method for the treatment of mammals to control the amount or activity of the replication initiator protein complex or subunits thereof, so as to alter the adverse consequences of such presence or activity.

It is a still further object of the present invention to provide a method for the treatment of mammals to control the amount or activity of the replication initiator protein complex or its subunits, so as to treat or avert the adverse consequences of invasive, spontaneous or idiopathic pathological states.

It is a still further object of the present invention to provide pharmaceutical compositions for use in therapeutic methods which comprise or are based upon the replication initiator protein complex, its subunits, their binding partner(s), or upon agents or drugs that control the production, or that mimic or antagonize the activities of the replication initiator protein complex/subunits.

Other objects and advantages will become apparent to those skilled in the art from a review of the ensuing description which proceeds with reference to the following illustrative drawings.

BRIEF DESCRIPTION OF THE DRAWINGS

FIG. 9 demonstrates that copurification of RIP60 and RIP100 from HeLa cell nuclear extract. Fractions from the first oligonucleotide affinity column that exhibited maximal RIP60 DNA binding activity were pooled, dialyzed, and applied to a second ATT DNA affinity column. Fractions eluted by a continuous salt gradient from 0.2 to 1.0M KCl were first assessed for RIP60 binding by gel shift assays; selected fractions from the portion of the gradient that encompassed RIP60 binding were then analyzed for protein constituents by SDS-PAGE and silver staining (panel 9A), specific RIP60 DNA binding by gel mobility shift assays with the ATT oligonucleotide as probe (GSC, panel 9B), ATP-dependent DNA helicase activity (panel 9C), and covalent labeling with [alpha-$^{32}$P]ATP (panel 9D). The DNA helicase assay was performed as in FIG. 7; the covalent radiolabeling of RIP100 was accomplished as described in FIG. 8. Molecular weight markers visualized by silver staining are indicated in panel A in kilodaltons.

DETAILED DESCRIPTION

Figure 1:
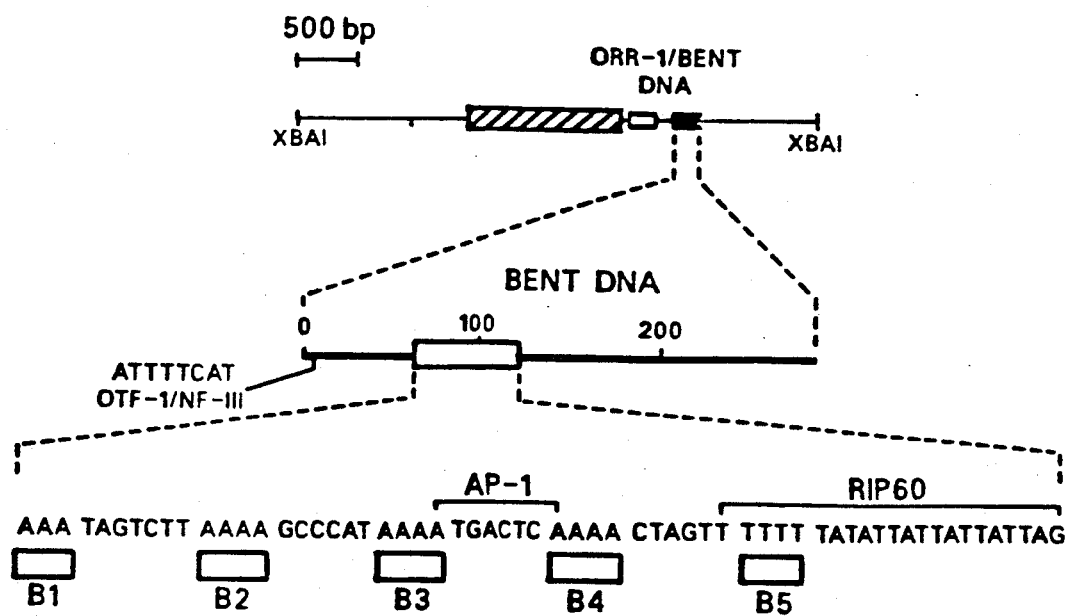
FIG. 1 is a graph demonstrating that the dhfr origin region contains stably bent DNA. Depicted is a schematic representation of the 4.3 kb Xba I dhfr origin fragment that encompasses a site for initiation of bidirectional DNA synthesis (hatched box), the repetitive element ORR-1, and the 280 bp Hae III fragment that includes stably bend DNA (for details concerning these DNA sequences, see Caddle et al., 1990). Sequence-directed DNA bending in this region is a result of five oligo $dA_{3-4}$ tracts (designated bend elements B1–B5, open boxes) phased precisely 10 bp apart. A consensus core binding site for AP-1 (TGACTCA) is located between bend elements B2 and B3. The binding site for RIP60 as delineated by DNase I footprinting experiments is indicated (see FIG. 2). Purified OTF-1/NFIII recognizes the indicated, sequence at the immediate 5' end of the 280 bp Hae bent DNA fragment.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual" (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

The term "stimulus" and its plural as used herein are intended to apply to invasive events such as cancer and viral infection, as well as conditions caused by wounding, and to idiopathic or spontaneous states that may for example, originate from cellular or metabolic derangements or other causes.

The terms "replication initiator protein complex", "protein complex/subunit(s)", "protein subunit(s)", "protein fraction(s)", "RIP60" and "RIP100" may be used herein interchangeably, and as used throughout the present application and claims refer to protein material having the profile of activities set forth herein and in the Claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "replication initiator protein complex", "protein complex/subunit(s)", "protein fraction(s)", "protein subunits", "RIP60" and "RIP100" are intended to include within their scope proteins specifically recited herein as well as all substantially homologous analogs and allelic variations.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the $-10$ and $-35$ consensus sequences.

A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes. For instance, alpha-factor, a native yeast protein, is secreted from yeast, and its signal sequence can be attached to heterologous proteins to be secreted into the media (See U.S. Pat. No. 4,546,082, EpO 0 116 201, publication date 12 Jan. 1983; U.S. patent application Ser. No. 522,909, filed 12 Aug. 1983). Further, the alpha-factor leader and its analogs have been found to secrete heterologous proteins from a variety of yeast, such as Saccharomyces and Kluyveromyces, (EPO 88312306.9 filed 23 Dec. 1988; U.S. patent application Ser. No. 139,682, filed 30 Dec. 1987, and EPO Publication No. 0 301 669, publication date 1 Feb. 1989).

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells, containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 50% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A composition comprising "A" (where "A" is a single protein, DNA molecule, vector, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

An "antibody" is any immunoglobulin, including antibodies and fragments thereof, that binds a specific epitope. The term encompasses, inter alia, polyclonal, monoclonal, and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. (The disclosures of the art cited herein are hereby incorporated by reference.) Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The phrase "substantially simultaneously" is used herein to mean within a time period sufficient to produce concurrent results; e.g., cellular lysis as a result of administration and amelioration or prevention of symptoms of pathology that may occur as a result of that lysis by administration of an appropriate anti-replication initiator protein complex antibody, peptide analog, other homolog, or a subcombination or combination thereof, as described herein.

The phrase "pharmaceutically acceptable" refers to molecular entities and compositions that are physiologically tolerable and do not typically produce an allergic or similar untoward reaction, such, as gastric upset, dizziness and the like, when administered to a human.

The phrase "therapeutically effective amount" is used herein to mean an amount sufficient to prevent, and preferably reduce by at least about 30 percent, more preferably by at least 50 percent, most preferably by at least 90 percent, a clinically significant change in the S phase activity of a target cellular mass, or other feature of pathology such as for example, elevated blood pressure, fever or white cell count as may attend its presence and activity.

In its primary aspect, the present invention concerns the isolation and identification of a newly discovered particular factor hereinafter referred to as the replication initiator protein complex, and its subunits named by the applicants herein RIP60 and RIP100, that has been found to be present in higher eukaryotes such as mammals, and that participates in the initiation of cell division.

As described herein the invention is the first instance of the isolation and purification of a replication initiator for higher animals and represents a significant finding that will lead to a greater understanding and control of cell division and its consequent effects on cellular stability and health.

The replication initiator protein complex comprises a protein material in purified form that as its primary affirmative characteristics, is capable of origin-specific DNA binding activity, and that exhibits ATP-dependent DNA helicase activity. Specifically, the present complex binds to the dhfr origin region of Chinese hamster cells adjacent to stably bent DNA, and to domain B of the yeast cell ARS1 region. The present protein complex also exhibits the characteristic that it is largely inactive in cells that are not undergoing division and appears as yet to play no role in cellular activity during such phases of the cell cycle.

In a further aspect of the invention the individual subunits have been purified and are found to comprise protein fractions of about 60 kD and 100 kD size, the former appearing to be primarily responsible for origin-specific DNA binding, and the latter involved with ATP-dependent DNA helicase activity. As described earlier, the commencement of S phase activity as understood, requires the nuclear DNA to commence its division to facilitate the formation of additional complementary strands, and thus division likewise requires that the normally double standard conformation of the DNA must be unwound. Both of these activities are necessary for cell division to commence and the interruption or inhibition of either function could block further replication activity.

Accordingly, the present invention extends to a replication initiator subunit comprising a proteinaceous material in purified form that is capable of binding to origin-specific DNA to promote cell replication. More particularly this subunit is an origin-specific DNA binding protein having a molecular weight of about 60 kD that is capable of binding to the origin region of the dhfr gene of Chinese hamster cell at a site adjacent to stably bent DNA, and can bind to domain B of the yeast cell ARS1 region.

A further replication initiator subunit of the present invention comprises a proteinaceous material in purified form that is capable of initiating DNA helicase activity. This subunit is an ATP-dependent DNA helicase and is about 100 kD in size. Its helicase activity was also established by standard oligonucleotide displacement assays as presented hereinafter.

The proteins identified herein are believed to serve as replication factors with a large number of higher eukaryotic cells such as mammalian cells, as the test models investigated herein have been extensively studied and proved to be broadly representative of other known replication initiation sites.

The present invention extends to the preparation of the protein complex and its respective subunits, by the incubation of nuclear material or extracts thereof with the origin of replication of a eukaryotic gene or cell, all as described both earlier and later on herein.

Representative genes or cells comprise the dhfr region of CHOC cells and the yeast ARS1 region, however it is understood that other cells and genes offering a similar environment would be suitable, so that the present invention should not be limited to the test models presented herein.

Likewise, and as discussed in greater detail herein, the preparation of the protein complex and its subunits may proceed by means of known recombinant means, and such recombinantly prepared proteins are considered within the scope of the present invention.

Thus, in one embodiment, the present invention contemplates a method of ameliorating conditions caused by cells or other pathogens that thrive while undergoing cell division, by administering to a patient in need of such therapy a therapeutically effective amount of an anti-protein complex/subunit antibody. Preferred therapeutically effective amounts for the agents used herein as active ingredients include those described hereinafter.

As discussed earlier, the protein complex/subunit or its binding partner(s) or other ligands or agents exhibiting either mimicry or antagonism to the protein complex/subunit or control over its production, may be prepared in pharmaceutical compositions, with a suitable carrier and at a strength effective for administration by various means to a patient having a viral infection, cancer, pre-cancerous lesion or other like pathological derangement, for the treatment thereof. A variety of administrative techniques may be utilized, among them parenteral techniques such as subcutaneous, intravenous and intraperitoneal injections, catheterizations and the like. Average quantities of the protein complex or its subunits may vary and in particular should be based upon the recommendations and prescription of a qualified physician or veterinarian.

Also, antibodies including both polyclonal and monoclonal antibodies, and drugs that modulate the production or activity of the protein complex and/or its subunits may possess certain therapeutic applications and may thus be utilized for the purpose of treating neoplasia, viral infection or the like. In particular, the protein complex or its subunits may be used to produce both polyclonal and monoclonal antibodies to themselves in a variety of cellular media, by known techniques such as the hybridoma technique utilizing, for example, fused mouse spleen lymphocytes and myeloma cells.

The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,4,27,783; 4,444,887; 4,451,570; 4,466,917; 4,472,500; 4,491,632; 4,493,890.

Panels of monoclonal antibodies produced against protein complex/subunit peptides can be screened for various properties; i.e., isotype, epitope, affinity, etc. Of particular interest are monoclonal antibodies that neutralize the activity of the protein complex or its subunits. Such monoclonals can be readily identified in protein complex activity assays. High affinity antibodies are also useful in immunoaffinity purification of native or recombinant protein complex.

Preferably, the anti-protein complex/subunit antibody used in the therapeutic methods of this invention is an affinity purified polyclonal antibody. More preferably, the antibody is a monoclonal antibody (mAb). In addition, it is preferable for the anti-protein complex/subunit antibody molecules used herein be in the form of Fab, Fab', F(ab')$_2$ or F(v) portions of whole antibody molecules.

Preferred monoclonal antibodies display an immunoreactivity for the protein complex/subunit that is similar to that of those produced by the above-described hybridomas. As used herein, the term "immunoreactivity" in its various grammatical forms refers to the concentration of antigen required to achieve a 50% inhibition of the immunoreaction between a given amount of the antibody and a given amount of the antigen. That is, immunoreactivity is the concentration of antigen required to achieve a $B/B_0$ value of 0.5, where $B_0$ is the maximum amount of antibody bound in the absence of competing antigen and B is the amount of antibody bound in the presence of competing antigen, and both $B_0$ and B have been adjusted for background. See Robard, Clin. Chem., 20:1255–1270 (1974).

In another particular embodiment, the therapeutic method of the present invention comprises administering a therapeutically effective amount of an anti-protein complex/subunit antibody, preferably an affinity-purified polyclonal antibody, and more preferably a mAb. In addition, it is preferable for the anti-protein complex/subunit antibody molecules used herein be in the form of Fab, Fab', F(ab')$_2$ or F(v) portions or whole antibody molecules. Preferably, the amount of anti-protein complex/subunit antibody administered is sufficient to reduce by at least about 30 percent, preferably by at least 80 percent, S phase activity of the target cells against which the antibody is administered. As previously discussed, patients capable of benefiting from this method include those suffering from cancer, a pre-cancerous lesion, a viral infection or other like pathological derangement. Methods for isolating the protein complex/subunit and inducing anti-protein complex/subunit antibodies and for determining and optimizing the ability of an anti-protein complex/subunit antibody to inhibit the binding of protein complex/subunit to the nuclear material of the target cells, and thereby inhibit protein complex/subunit-induced cell replication are all well-known in the art.

Methods for producing polyclonal anti-polypeptide antibodies are well-known in the art. See U.S. Pat. No. 4,493,795 to Nestor et al. A monoclonal antibody, antibody molecules, can be prepared using the hybridoma technology described in *Antibodies—A Laboratory Manual,* Harlow and Lane, eds., Cold Spring Harbor Laboratory, New York (1988), which is incorporated herein by reference. Briefly, to form the hybridoma from which the monoclonal antibody composition is produced, a myeloma or other self-perpetuating cell line is fused with lymphocytes obtained from the spleen of a mammal hyperimmunized with a protein complex/subunit-binding portion thereof, or protein complex/subunit, or an origin-specific DNA-binding portion thereof.

It is preferred that the myeloma cell line be from the same species as the lymphocytes. Typically, a mouse of the strain 129 G1X+ is the preferred mammal. Suitable mouse myelomas for use in the present invention include the hypoxanthine-aminopterin-thymidine-sensitive (HAT) cell lines P3X63-Ag8.653, and Sp2/0-Ag14 that are available from the American Type Culture Collection, Rockville, Md., under the designations CRL 1580 and CRL 1581, respectively.

Splenocytes are typically fused with myeloma cells using polyethylene glycol (PEG) 6000. Fused hybrids are selected by their sensitivity to HAT. Hybridomas producing a monoclonal antibody useful in practicing this invention are identified by their ability to immunoreact with the present protein complex/subunit and their ability to inhibit S phase activity in target cells.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Media useful for the preparation of these compositions are both well-known in the art and commercially available and include synthetic culture media, inbred mice and the like. An exemplary synthetic medium is Dulbecco's minimal essential medium (DMEM; Dulbecco et al., *Virol.* 8:396 (1959)) supplemented with 4.5 gm/l glucose, 20 mm glutamine, and 20% fetal calf serum. An exemplary inbred mouse strain is the Balb/c.

Methods for producing monoclonal anti-protein complex/subunit antibodies are also well-known in the art. See Niman et al., *Proc. Natl. Acad. Sci. USA.* 80:4949–4953 (1983). Typically, the present protein complex/subunit or a peptide analog is used either alone or conjugated to an immunogenic carrier, as the immunogen in the before described procedure for producing anti-protein complex/subunit monoclonal antibodies. The hybridomas are screened for the ability to produce an antibody that immunoreacts with the protein complex/subunit peptide analog and the present protein complex/subunit.

Patients at a risk for or exhibiting the symptoms of certain cancers and viral infections are capable of benefiting from the administration of therapeutic modalities known in the art to prevent or ameliorate those symptoms. Thus, the present invention contemplates administering a therapeutically effective amount of an anti-protein complex/subunit antibody, protein complex/subunit peptide analog, a subcombination or combination thereof, either alone or substantially simultaneously with therapeutic administration of a modality known to prevent or treat the symptoms or the pathology. For instance, such antibodies, analogs or the like may be administered in conjunction with other known chemotherapeutic agents in the instance of cancer, or antiviral agents in the instance of viral attack.

For example, a patient exhibiting the symptoms of neoplastic attack may be treated with an antineoplastic agent such as doxorubicin, daunorubicin or the like. In such instance therefore, a preferred therapeutic method might include administering a therapeutically effective amount of an anti-protein complex/subunit antibody, a peptide analog or subcombination thereof as described herein, substantially simultaneously with administering the prescribed amount of the antineoplastic agent. The prescribed amount of antineoplastic agents generally recognized as safe for administration to humans is an amount well-known in the art and varies, as is also well-known, with the antineoplastic agent and the type of cancer being treated.

In a preferred embodiment, administration of an anti-protein complex/subunit antibody, peptide analog or combination thereof as described herein may occur within about 48 hours, preferably within about 12–36 hours, more preferably within about 2–8 hours and most preferably substantially concurrently with administration of the antiviral or antineoplastic agent.

The present invention further contemplates therapeutic compositions useful in practicing the therapeutic methods of this invention. A subject therapeutic composition includes, in admixture, a pharmaceutically acceptable excipient (carrier) and one or more of an anti-protein complex/subunit antibody, or polypeptide analog thereof, as described herein as an active ingredient. In preferred embodiments, the composition comprises an antibody or antigen capable of inhibiting either the origin-specific binding of the present protein complex/subunit to nuclear material of the target cell, or the initiation of DNA helicase activity by the protein complex/subunit.

The preparation of therapeutic compositions which contain polypeptides or antibody molecules as active ingredients is well understood in the art. Typically, such compositions are prepared as injectables, either as liquid solutions or suspensions, however, solid forms suitable for solution in, or suspension in liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide or antibody can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic polypeptide- or antibody-containing compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner, compatible with the dosage formulation, and in a therapeutically effective amount. The quantity to be administered depends on the subject to be treated, capacity of the subject's immune system to utilize the active ingredient, and degree of inhibition or neutralization of protein complex/subunit binding capacity desired. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

As used herein, "pg" means picogram, "ng" means nanogram, "ug" or "$\mu$g" mean microgram, "mg" means milligram, "ul" or "$\mu$l" mean microliter, "ml" means milliliter, "l" means liter.

It is further intended that protein complex/subunit analogs may be prepared from nucleotide sequences of the protein complex/subunit derived within the scope of the present invention. Analogs, such as fragments, may be produced, for example, by pepsin digestion of protein complex/subunit material. Other analogs, such as muteins, can be produced by standard site-directed mutagenesis of protein complex/subunit coding sequences. Analogs exhibiting "protein complex/subunit activity" may be identified by known in vivo and/or in vitro assays.

As mentioned above, a DNA sequence encoding protein complex/subunit can be prepared synthetically rather than cloned. The DNA sequence can be designed with the appropriate codons for the protein complex/subunit amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, *Nature*, 292:756 (1981); Nambair et al., *Science*, 223:1299 (1984); Jay et al., *J. Biol. Chem.*, 259:6311 (1984).

Synthetic DNA sequences allow convenient construction of genes which will express protein complex/subunit analogs or "muteins". Alternatively, DNA encoding muteins can be made by site-directed mutagenesis of native protein complex/subunit genes or cDNAs, and muteins can be made directly using conventional polypeptide synthesis.

Site-directed mutagenesis is generally used to create analogs from a complete coding sequence. Site-directed mutagenesis is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques are hybridized with kinased synthetic primer at a temperature which permits hybridization of an exact match, but at which the mismatches with the original strand are sufficient to prevent hybridization. Plaques which hybridize with the probe are then picked, cultured, and the DNA recovered.

A general method for site-specific incorporation of unnatural amino acids into proteins is described in Christopher J. Noren, Spencer J. Anthony-Cahill, Michael C. Griffith, Peter G. Schultz, *Science*, 244: 182–188 (April 1989). This method may be used to create analogs with unnatural amino acids.

The present invention also relates to a variety of diagnostic applications, including methods for detecting the presence of invasive stimuli by reference to their ability to elicit the activities which are affected by the present protein complex/subunit. As mentioned earlier, the protein complex/subunit can be used to produce antibodies to itself by a variety of known techniques, and such antibodies could then be isolated and utilized as in tests for the presence of S phase activity in suspect target cells.

As described in detail above, antibody(ies) to the protein complex/subunit can be produced and isolated by standard methods including the well known hybridoma techniques. For convenience, the antibody(ies) to the protein complex/subunit will be referred to herein as $Ab_1$ and antibody(ies) raised in another species as $Ab_2$.

The presence of protein complex/subunit activity in cells can be ascertained by the usual immunological procedures applicable to such determinations. A number of useful procedures are known. Three such procedures which are especially useful utilize either the protein complex/subunit labeled with a detectable label, antibody $Ab_1$ labeled with a detectable label, or antibody $Ab_2$ labeled with a detectable label. The procedures may be summarized by the following equations wherein the asterisk indicates that the particle is labeled, and "Rip" stands for the protein complex/subunit:

A. $Rip^* + Ab_1 = Rip^*Ab_1$
B. $Rip + Ab^* = RipAb_1^*$
C. $Rip + Ab_1 + Ab_2^* = RipAb_1Ab_2^*$

The procedures and their application are all familiar to those skilled in the art and accordingly may be utilized within the scope of the present invention. The "competitive" procedure, Procedure A, is described in U.S. Pat. Nos. 3,654,090 and 3,850,752. Procedure C, the "sandwich" procedure, is described in U.S. Pat. No. RE 31,006 and U.S. Pat. No. 4,016,043. Still other procedures are known such as the "double antibody," or "DASP" procedure.

In each instance, the protein complex/subunit forms complexes with one or more antibody(ies) or binding partners and one member of the complex is labeled with a detectable label. The fact that a complex has formed and, if desired, the amount thereof, can be determined by known methods applicable to the detection of labels.

It will be seen from the above, that a characteristic property of $Ab_2$ is that it will react with $Ab_1$. This is because $Ab_1$ raised in one mammalian species has been used in another species as an antigen to raise the antibody $Ab_2$. For example, $Ab_2$ may be raised in goats using rabbit antibodies as antigens. $Ab_2$ therefore would be anti-rabbit antibody raised in goats. For purposes of this description and claims, $Ab_1$ will be referred to as a primary or anti-protein complex/subunit antibody, and $Ab_2$ will be referred to as a secondary or anti-$Ab_1$ antibody.

The labels most commonly employed for these studies are radioactive elements, enzymes, chemicals which fluoresce when exposed to ultraviolet light, and others.

A number of fluorescent materials are known and can be utilized as labels. These include, for example, fluorescein, rhodamine and auramine. A particular detecting material is anti-rabbit antibody prepared in goats and conjugated with fluorescein through an isothiocyanate.

The protein complex/subunit or its binding partner(s) can also be labeled with a radioactive element or with an enzyme. The radioactive label can be detected by any of the currently available counting procedures. The preferred isotope may be selected from $^{14}C$, $^{131}I$, $^{3}H$, $^{125}I$ and $^{35}S$.

Enzyme labels are likewise useful, and can be detected by any of the presently utilized colorimetric, spectrophotometric, fluorospectrophotometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, $\beta$-glucuronidase, $\beta$-D-glucosidase, $\beta$-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

A particular assay system developed and utilized in accordance with the present invention is known as a receptor assay. In a receptor assay, the material to be assayed is appropriately labeled and then certain cellular test colonies are inoculated with a quantity of both the labeled and unlabeled material after which binding studies are conducted to determine the extent to which the labeled material binds to the cell receptors. In this way, differences in affinity between materials can be ascertained.

Accordingly, a purified quantity of the protein complex/subunit may be radiolabeled and combined, for example, with antibodies or other inhibitors thereto, after which binding studies would be carried out using for example, Chinese hamster dhfr origin region sequences as described herein. Solutions would then be prepared that contain various quantities of labeled and unlabeled uncombined protein complex/subunit, and cell samples would then be inoculated and thereafter incubated. The resulting cell monolayers are then washed, solubilized and then counted in a gamma counter for a length of time sufficient to yield a standard error of <5%. These data are then subjected to Scatchard analysis after which observations and conclusions regarding material activity can be drawn. While the foregoing is exemplary, it illustrates the manner in which a receptor assay may be performed and utilized, in the instance where the cellular binding ability of the assayed material may serve as a distinguishing characteristic.

In a further embodiment of this invention, commercial test kits suitable for use by a medical specialist may be prepared to determine the presence or absence of S phase activity or S phase activity capability in suspected target cells. In accordance with the testing techniques discussed above, one class of such kits will contain at least the labeled protein complex/subunit or its binding partner, for instance an antibody specific thereto, and directions, of course, depending upon the method selected, e.g., "competitive", "sandwich", "DASP" and the like. The kits may also contain peripheral reagents such as buffers, stabilizers, etc.

Accordingly, a test kit may be prepared for the demonstration of the presence or capability of cells for S phase activity, comprising:

(a) a predetermined amount of at least one labeled immunochemically reactive component obtained by the direct or indirect attachment of the present protein complex/subunit or a specific binding partner thereto, to a detectable label;
(b) other reagents; and
(c) directions for use of said kit.

More specifically, the diagnostic test kit may comprise:

(a) a known amount of the protein complex/subunit as described above (or a binding partner) generally bound to a solid phase to form an immunosorbent, or in the alternative, bound to a suitable tag, or plural such end products, etc. (or their binding partners) one of each;
(b) if necessary, other reagents; and
(c) directions for use of said test kit.

In a further variation, the test kit may be prepared and used for the purposes stated above, which operates according to a predetermined protocol (e.g. "competitive," "sandwich," "double antibody," etc.), and comprises:

(a) a labeled component which has been obtained by coupling the protein complex/subunit to a detectable label;
(b) one or more additional immunochemical reagents of which at least one reagent is a ligand or an immobilized ligand, which ligand is selected from the group consisting of:
   (i) a ligand capable of binding with the labeled component (a);

(ii) a ligand capable of binding with a binding partner of the labeled component (a);

(iii) a ligand capable of binding with at least one of the component(s) to be determined; and (iv) a ligand capable of binding with at least one of the binding partners of at least one of the component(s) to be determined; and (c) directions for the performance of a protocol for the detection and/or determination of one or more components of an immunochemical reaction between the protein complex/subunit and a specific binding partner thereto.

In accordance with the above, an assay system for screening potential drugs effective to modulate the activity of the protein complex/subunit may be prepared. The protein complex/subunit may be introduced into a test system such as the dhfr origin region of Chinese hamster cells or the ARS1 region of yeast cells, and the prospective drug may also be introduced into the resulting cell culture, and the culture thereafter examined to observe any changes in the activity of the protein complex/subunit, due either to the addition of the prospective drug alone, or due to the effect of added quantities of the known protein complex/subunit.

More particularly, a drug assay could be conducted by culturing a colony of test cells such as Chinese hamster CHOC 400 cell line containing the dhfr element, or the yeast cell line *Sacchromyces cerevesiae* defining the ARS1 region, which has a receptor for the protein complex/subunit, in a medium containing the protein complex/subunit. The drug under test could be added to the resulting culture and the reactivity of the protein complex/subunit with the receptor on the test cells could thereafter be measured to determine whether the prospective drug possessed any activity in the inhibition of the binding of the protein complex/subunit to the receptor.

The following examples set forth the details of the isolation and identification of the present protein complex and its subunits RIP60 and RIP100, and observations noted as to activity, defining both the distinctions and similarities in activity between the present protein complex and those factors identified earlier both by applicants and by others in the field. Naturally, the specific materials and techniques set forth hereinafter are exemplary only and may vary, so that the following is presented as illustrative but not restrictive of the present invention.

INTRODUCTION TO EXAMPLES

The replication of the Chinese hamster dihydrofolate reductases (dhfr) domain has been studied extensively. Pulse-labeling studies in synchronized CHOC 400 cells, which contain approximately 1000 copies of the dhfr replicon, show that replication of the amplified dhfr genes begins within a doublet of 6.1 kb eco R1 fragments termed ELF-F/ELF-F' (for early-labeled fragments F and F'). Strand-specific nucleosome condensation studies in methotrexate-sensitive CHO cells have shown that the origin of replication within the ELF-F/ELF-F' doublet functions in the absence of gene amplification, and transfection experiments with large lambda phage clones have shown that the dhfr origin is active when transferred to new chromosomal locations. Thus, the dhfr origin of replication from the ELF-F/ELF-F' region represents a suitable model system for delineating initiation of DNA synthesis within a typical mammalian replicon.

To identify sequences that may be involved in initiation at the dhfr origin, the nucleotide sequence of the origin region was determined, and these sequences were then surveyed for structural elements common to other origins of replication. Prominent among the features of the immediate dhfr origin region is a fragment of stably bent DNA that includes several consensus sequences for proliferation-specific transcription factors.

To investigate the mechanism by which the dhfr origin of replication is activated and to determine whether a particular protein or enzyme functions as an initiator of replication in eukaryotes including mammalian cells, the dhfr origin fragment that includes stably bent DNA was used to assay nuclear extracts from HeLa cells for DNA binding proteins that display the signature properties of initiation factors, i.e., origin-specific DNA binding and DNA helicase activity. The organization of the dhfr region and the recovery of RIP60 and RIP100 is set forth below.

EXPERIMENTAL PROCEDURES

The following procedures were used in the experiments set forth in the Examples. The details are presented below and may be referred to alone or in conjuction with the Figure descriptions as the Examples are reviewed.

DNA PLASMIDS AND OLIGONUCLEOTIDES

Plasmid pMC304 contain the 280 bp Hae III bent DNA fragment of the dhfr origin region cloned into the SmaI site of pUC12. This fragment spans residues 3342 to 3622 of the dhfr origin sequence as reported by Caddle et al. (1990); the bend elements B1-B5 displayed in FIG. 1 occupy residues 3415 to 3459. The bend 208 probe was generated by the polymerase chain reaction, and spans residues 3318 to 3526; the ORI oligonucleotide spans residues 3432 to 3502; the oligonucleotide BEND spans 3424 to 3457. The ORI, BEND and ATT oligonucleotide were synthesized on an Applied Biosystems DNA synthesizer and are comprised of the following sequences:

ORI:
5'..ATAAAATGACTCAAAACTAGTTTTTTATTATTATTATTAGTT...
3'..GTATTTTACTGAGTTTTGATCAAAAAAATAATAATAATAATCAA...

..CAAATTAGGAAGAAGCTTGCTTTACATG..3'
..GTTAATCCTTCTTCGAAC.....5'

BEND:
5'...GGGTCTAGAAAAGCCCATAAAATGACTCAAAACTAGTTTTTTCTAGA...3'
3'...CCCAGATCTTTTCGGGTATTTTACTGAGTTTTGATCAAAAAAGATCT...5'

TAA:

-continued

```
5'... GGAATTCACTCGGATCCT(AAT)15GAGTCGACG...3'
3'.....GAGCCTAGGA(TTA)15CTCAGTGC...5'
```

The H4 oligonucleotide represents sequences from the promoter region of the human histone H4 gene; its sequence is presented as oligonucleotide 1 in Dailey et all. (1988).

DNA BINDING ASSAYS

Gel mobility shift assays were performed essentially as described previously (Fried and Crothers, 1981) and generally utilized either 0.5 ng of labeled DNA fragment or 0.2 ng of oligonucleotide probe. The amounts of poly dI/poly dC and HeLa nuclear extract of chromatographic fraction included in specific reactions varied; with the 0.35M KCl DE or 0.5M KCl S-sepharose column fractions 1.0-2.0 ul of extract was assayed in the presence of 600 ug/ml poly dI/poly dC. Assays of fractions from the oligonucleotide columns contained 0.25-1.0 ul protein in the presence of 40-150 ug/ml poly dI/poly dC. For the DNase I footprinting assays, 0.5 ng of the Eco RI-Bam HI fragment from pMC304, either 3' or 5' end labeled at the Eco RI site was used as probe. Digestion with DNase I was as described (Galas, D., & Schmitz, A. (1978) NUCL. ACIDS. RES., 5, 3157-3170). The digestion products were analyzed on an 8% polyacrylamide, 50% urea gel in 0.5×TBE and, after autoradiography, the regions protected from DNase I digestion were located by comparison to a G chemical sequencing reaction (Maxam, A. M., & Gilbert, W. (1980). METH. ENZYMOL. 65, 499-560) of the same probe.

CHROMATOGRAPHY OF HeLa CELL NUCLEAR EXTRACTS

HeLa nuclear extracts were prepared as described by Digman et al. (1983). All chromatography buffers (BC) consisted of 20 mM Hepes (7.9), 50% glycerol, 0.02% NP40, 0.5 mM PMSF, 0.5 mM DTT and varying concentrations of KCl. 100 ml of HeLa nuclear extract (12 mg/ml) was loaded onto a 10 ml CM sepharose (Pharmacia) column at a flow rate of 12 column volumes per hour, and the flow through was directly applied to a 40 ml DE sepharose (Pharmacia) column at 3 column volumes per hour.

RIP60 was eluted from the DE sepharose column with BC buffer containing 0.35M KCl and the pooled step fractions (296 mg of protein) were dialyzed against BC50 and applied to a 7 ml S sepharose column at 4 column volumes per hour. After washing with 2.5 column volumes of BC50, a 0.2M KCL step fraction was collected prior to elution of RIP60 with BC500. The pooled 0.5M KCl fractions (12.2 mg protein) were dialyzed against BC100 and applied at a rate of 15 column volumes per hour to a 1 ml ATT-oligonucleotide column. After washing with 6 column volumes of BC100, 6 ml of BC200 was applied, followed by a 6 column volume linear salt gradient from 0.2M to 1.0M KCl. The column was washed with 3 column volumes of M KCl to completely elute all of the RIP60/RIP100 protein.

Gradient fractions that exhibited RIP60 binding activity in gel shift assays using the ATT oligonucleotide as probe were pooled, dialyzed against BC100, reapplied to a 0.4 ml ATT oligonucleotide column and eluted as before. Protein concentrations were monitored throughout the purification using the Bio Rad protein assay (Biorad). RIP60 binding activity was quantitated using 0.2-2.0 ng of ATT oligonucleotide probe and various dilutions of protein fraction in gel shift assays. Shifted, probe was excised from the gel after localization by autoradiography, counted in Beckman Model LS 1801 scintillation counter and compared to the cpm of known amounts of free probe to determine the amount of RIP60 binding activity per unit volume at each step of the purification. Proteins were visualized by SDS-PAGE and silver staining using the Rapid Ag Kit (ICN Biochemicals).

UV CROSSLINKING

UV crosslinking experiments were performed essentially as described by Chodash, L. A. et al. [(1986), MOL. CELL. BIOL., 4, 2455-2466] and Wu, C. et al. [(1987), SCIENCE, 258, 1247-1253], with modifications as described by Dailey, L. S. et al. [(1988), GENES AND DEVELOPMENT, 2, 1700-1712]. The DNA probe was made by annealing the oligo 5'-CGTCGACTCATTATTATTA-3' to the top strand of the ATT oligonucleotide. The DNA was then filled in with Klenow fragment in the present of [alpha-$^{32}$P]dATP and 50 uM each of dCTP, dGtp, and deoxyuridine triphosphate. After a 30 minute incubation at room temperature, the reaction was chased with 50 uM of cold dATP for an additional 30 minutes.

Approximately 0.2 ng of uniformly labeled probe was incubated with RIP60 protein (which had been cycled twice over the ATT oligonucleotide column) and various unlabeled oligonucleotide competitors in a 10 ul reaction volume. After UV irradiation for 20 minutes and nuclease digestion, the samples were boiled in SDS-PAGE loading buffer and resolved by electrophoresis on a 10% SDS stacking gel with molecular weight markers (Sigma 6H). The gel was fixed and stained to visualize the protein markers. The gel was then dried and subjected to autoradiography to visualize labeled polypeptides.

DNA HELICASE ASSAY

The DNA helicase assay was modified from that described by Lahue and Matson (1988). The substrate was prepared by end labeling the universal sequencing primer annealed to single stranded M13mp18 DNA (Pharmacia) with [alpha-$^{32}$P]dATP and Klenow fragment. The labeled DNA hybrid was purified by gel filtration chromatography on CL-4B Sepharose.

The standard reaction (20 ul) contained 40 mM Tris-HCl (pH 7.5), 2 mM MgCl$_2$·6 mM DTT, 50 ug/ml nuclease free BSA (Boehringer Mannhiem), approximately 2 uM helicase substrate, and 1.0 to 1.5 ul protein extract. Reactions were mixed on ice, incubated at 37° C. for 15 min. and were then stopped by the addition of 10 ul of 50 mM EDTA, 40% glycerol, 0.6% SDS, 0.1% bromphenol blue, 0.1% xylene cyanole. The reaction products were resolved on 8% neutral polyacrylamide gels in 0.5X TBE and visualized by autoradiography.

COVALENT LABELING WITH [alpha-P$^{32}$]ATP

Covalent labeling of RIP100 was performed essentially as described by Sopta, M. et al. [(1980), NATURE, 341, 410-414]. Briefly, 2 uls of protein fraction from the final oligonucleotide affinity column were incubated in a 10 ul reaction volume in the presence of 60 mM KCl, 1 mM MgCl$_2$·6 mM DTT and 1 ul of [alpha-$^{32}$P]dATP (specific activity 800 Ci/mmole, New England Nuclear) for 1 minute on ice and 1 minute at room temperature before addition of SDS-PAGE loading buffer. For NTP competition experiments, 0.1 mM of unlabeled NTPS were also present in the reactions. The samples were boiled and resolved by SDS-PAGE along with protein molecular weight markers (Sigma 6H). After electrophoresis, the proteins were fixed and silver stained (ICN Biochemicals) to visualize the molecular weight markers. The gel was then dried and subjected to autoradiography against XAR-5 film (Kodak) at room temperature.

EXAMPLE 1

The dhfr Origin Region Contains Bent DNA

In this experiment, it was sought to determine whether the proposed test dhfr origin region contains stably bent DNA, as the presence of the latter was believed to be involved with origin-specific interaction with the initiator to take place.

The dhfr origin region was previously surveyed for stably bent DNA by a 2D gel electrophoresis technique (Anderson, J. N. (1986). NUCL. ACIDS RES., 14, 8513–8533). A single 280 bp Hae III fragment was identified that migrated approximately 19% slower than predicted in polyacrylamide gels (Caddle, M. S. et al., (1990). J. MOL. BIOL. 211, 19–33). Cloning and DNA sequencing located the bent DNA to the 3' end of the 1.8 kb Bam H1-Hind III fragment that contains a replication initiation site as identified by an "in gel" renaturation analysis (Leu, T. H., & Hamlin, J. L. (1989). MOL. CELL. BIOL., 9, 523–531) and strand-specific hybridization studies with Okazaki fragments (Burhans, W. C. et al., CELL, in preparation). Computer-aided examination of these DNA sequences indicated that bending of the 280 bp fragment was likely due to the presence of five periodic tracts of A$_{(3-4)}$ which are spaced precisely 10 bp apart (see sequences labeled B1-B5 in FIG. 1).

To ascertain if these sequences represented the bending element of the 280 bp Hae III fragment, a double stranded oligonucleotide encompassing the B1-B5 sequences was cloned into the plasmid pBEND (Zwieb, C. J. et al. (1989). GENES AND DEVELOPMENT, 3, 606–611. Cyclic permutation assays confirmed that bend elements, B1-B5 were sufficient to induce stable DNA bending in new sequence contexts (Caddle, M. et al., (1990), accepted for publication).

Analysis of the fragment that contains the bent DNA sequences also revealed several nearby consensus sequences for transcriptional activators, including one potential binding site for AP1 (Angel, P. et al., (1987). CELL, 49, 729–739) and two potential binding sites for OTF1/NFIII. The cellular transcription factor OTF1/NFIII regulates expression of the histone H2B gene during the S phase and also potentiates efficient initiation of adenovirus DNA replication in vitro (O'Neill, E. A. et al., (1988). SCIENCE, 241, 1210–1213). Gel shift and DNA binding competition experiments using various portions of the bent DNA fragment as probe show that the ATTTTCAT sequence element at the immediate 5' end of the 280 bp Hae III fragment is able to bind purified OTF1/NFIII (see FIG. 1), whereas the related sequence, ATTGACAT, which is located in the reverse orientation near the 3' end, does not (data not shown).

Figures 2A, 2B:
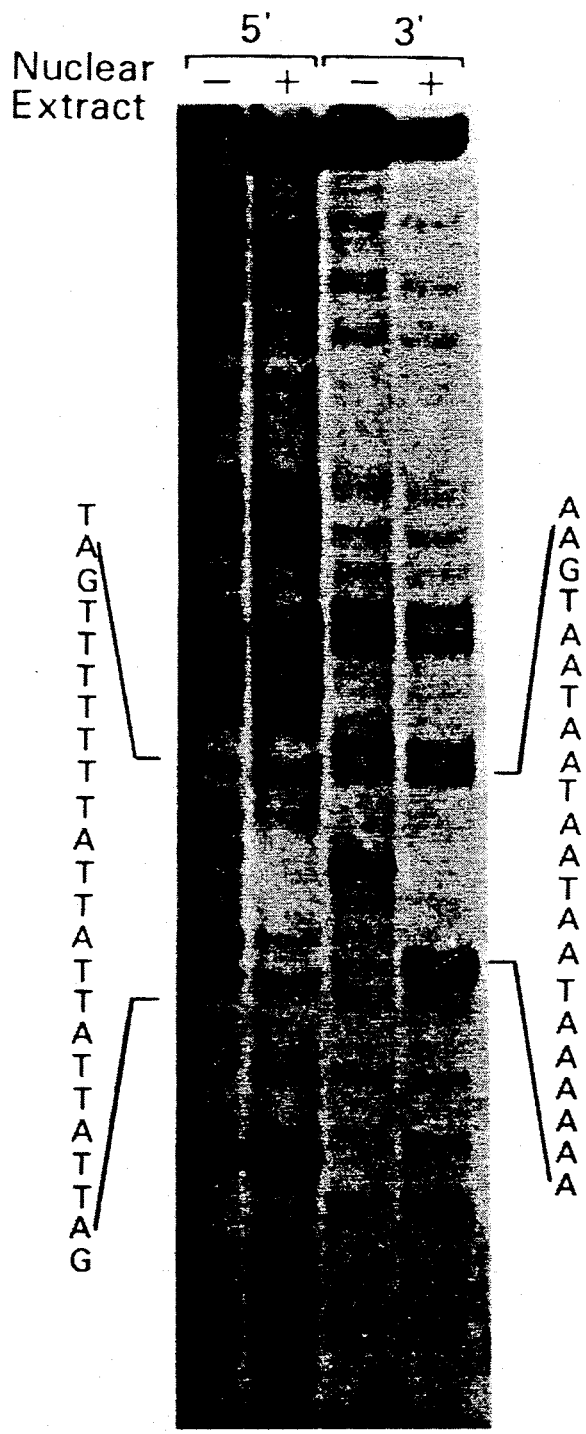
FIG. 2 illustrates DNAse I footprint of protein-DNA interactions in the bent DNA region. 2A) The bent DNA region was excised from plasmid pMC304, labeled at the Eco R1 site with either polynucleotide kinase (5'probe) or Klenow fragment (3' probe), and the resulting probes were incubated with DNase I in the presence (+) or absence (−) of HeLa cell nuclear extract as described in the Experimental Procedures. The regions protected from DNase I digestion were located by comparison to a G chemical sequencing reaction (Maxam and Gilbert, 1980) of the same probe (not shown) on denaturing polyacrylamide gels. 2B) Schematic representation of the DNA sequences protected from DNase I by HeLa cell nuclear extract. The sequences identified by footprint analysis (panel A) include bend element B5 and an ATT-rich motif that abuts the immediate 3' end of the bent DNA sequences.

To identify novel protein factors that interact with other DNA sequences within the 280 bp Hae III bent DNA fragment, this fragment was used as a probe in DNAse I protection assays using Hela cell nuclear extracts. As shown in FIG. 2, a distinct region on both strands was clearly protected from DNase I cleavage. Interestingly, the protected region, which contains repeated ATT motifs, is located immediately adjacent to the 3' end of the bent DNA sequences. The position of this binding site was particularly intriguing since it is reminiscent of the structural organization of a variety of well characterized replication origins in which a specific initiator protein binds adjacent to bent or AT-rich DNA sequences. For this reason, it was determined to purify and further characterize the (ATT)$_n$-binding factor.

EXAMPLE 2

Purification of the ATT-binding Factor, RIP60

The factor that binds the dhfr ATT-rich repeats was purified to near homogeneity by a combination of conventional ion exchange and oligonucleotide affinity chromatography. Because competition experiments using the DNase I protection assay showed that an oligonucleotide containing fifteen tandem ATT repeats was an effective competitor for binding of the Hela cell factor, this oligonucleotide (designated ATT) was used to prepare the oligonucleotide affinity column. The data developed from the purification of RIP60 is set forth in Table 1, below.

TABLE 1

PURIFICATION OF RIP60

| PROTEIN FRACTION | TOTAL PROTEIN (MGS) | TOTAL UNITS | SPECIFIC ACTIVITY (UNITS/MG PROTEIN) | FOLD PURIFICATION |
|---|---|---|---|---|
| NUCLEAR EXTRACT | 1261 | 42,320 | 34 | 1.0 |
| CM-FT/0.35KLC DE | 296 | 29,274 | 99 | 2.9 |
| 0.5M KCl S-SEPHAROSE | 12.2 | 2,271 | 186 | 5.5 |
| OLIGO COLUMN 1 | .03 | 1,545 | 51,500 | 1,515 |
| OLIGO COLUMN 2 | .002 | 588 | 294,000 | 8,647 |

Purification of RIP60, the ATT-binding activity, from HeLa cell nuclear extracts. The DNA binding activity that recognizes the ATT-rich repeats from the dhfr origin region was purified from HeLa cell nuclear extracts by a combination of ion exchange and DNA affinity chromatography. Purification was monitored by gel electrophoresis mobility shift assays using the ATT oligonucleotide as probe. One unit of binding activity represents that amount of fraction required to quantitatively bind 10 fmol of probe under gel mobility shift conditions.

Figure 3A:
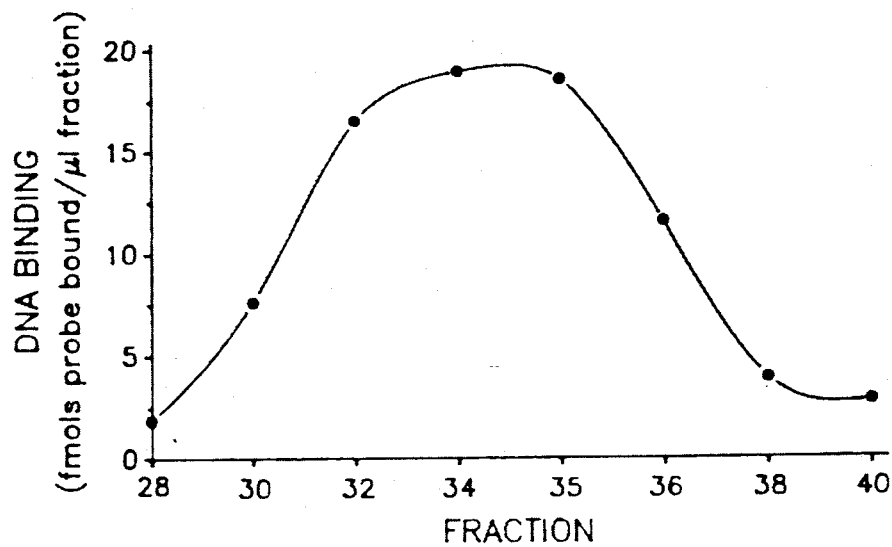
FIG. 3 demonstrates that the ATT-binding activity coelutes with the 60 kd protein. The protein factor(s) that bind specifically to the ATT-rich repeats from the dhfr origin region were purified from HeLa cell nuclear extracts as described in Table 1, later on herein. Column fractions eluted from the second oligonucleotide affinity column by a 0.2 to 1M KCl gradient that exhibited specific origin DNA binding (panel 3A) were analyzed along with protein molecular weight markers by SDS-PAGE and silver staining (panel 3B). The 60 kD polypeptide that coelutes with the ATT-binding activity is designated RIP60.
Figure 3B:
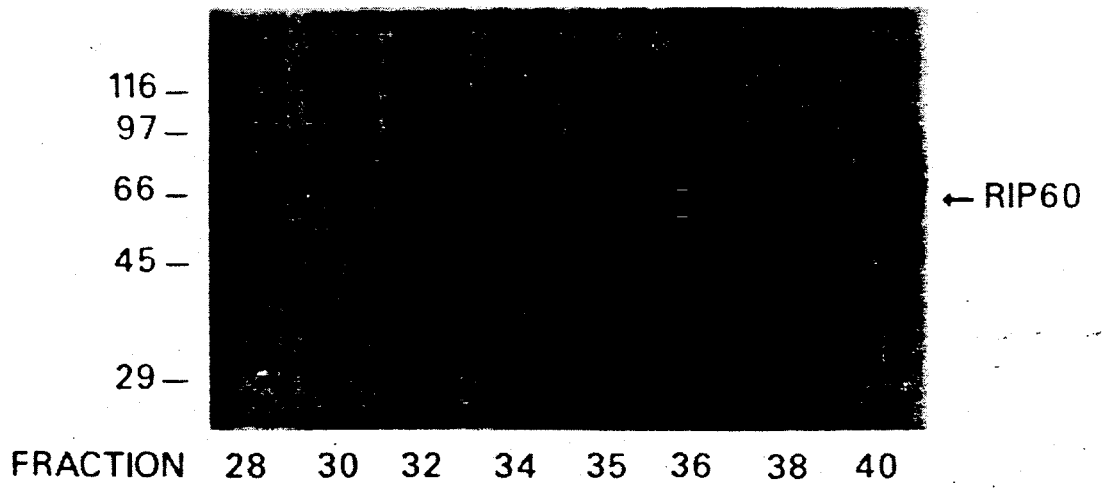

As can be seen from Table 1, the ATT-binding factor was purified nearly 9,000 fold as assessed by quantitative DNA binding assays using the ATT oligonucleotide as probe 1. DNase I footprinting was performed with the most purified DNA affinity column fraction on the original dhfr bent DNA probe to confirm that the purified factor was responsible for the footprint originally detected in the crude nuclear extract. The pattern of DNase I protection was identical using either nuclear extract (FIG. 2) or the final purified protein preparation (data not shown). After two cycles over the ATToligoaffinity column, a major polypeptide of approximately 60 kD that coeluted with the DNA binding activity was observed on silverstained SDS-polyacrylamide gels (FIG. 3).

To confirm that the 60 kD protein represented the ATT binding activity, UV protein-DNA crosslinking experiments were performed. When proteins bound to uniformly-labeled DNA probes are irradiated with UV light, covalent adducts are formed between the amino acids of the bound factor and the radioactive residues of the probe (Chodash. L. et al., 1986; Wu et al., 1987). When excess probe which is not directly linked to the bound factor is trimmed away by nuclease digestion, the bound factor remains radiolabeled, and it can be visualized by SDS-PAGE and autoradiography. The specificity of the protein-DNA interaction is assessed by including various DNA competitors during the incubation of the factor with the probe. Specific competitors prevent binding of the factor to the probe, and therefore prevent radiolabeling of the protein during UV irradiation.

Figure 4:
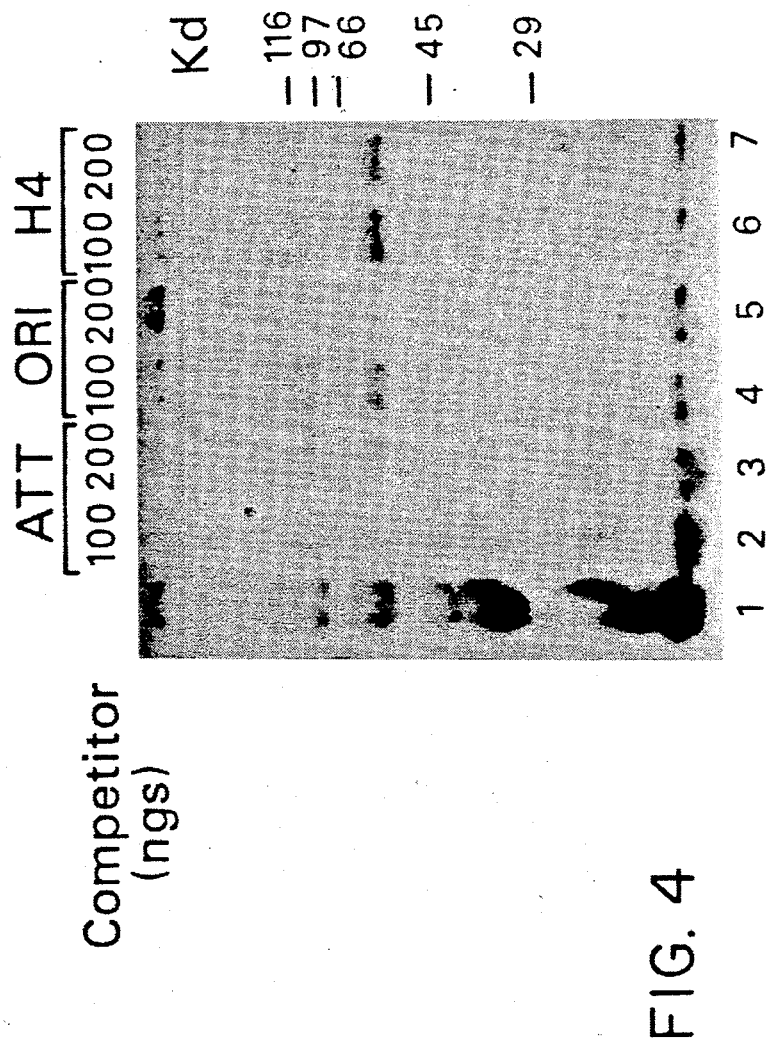
FIG. 4 demonsrates that protein-DNA crosslinking identified RIP60 as the ATT-binding activity. A uniformly labeled ATT oligonucleotide probe was incubated with a RIP60 fraction from the second oligonucleotide column in the presence or absence of the indicated amounts of competitor DNA. After irradiation with UV light, the samples were digested with nuclease and processed for SDS-PAGE, silver staining, and autoradiography as described in the Experimental Procedures. Autoradiography shows that the DNA binding activity that is specifically inhibited by either the ATT (lanes 2 and 3) or ORI (lanes 4 and 5) oligonucleotide competitors, but not the H4 oligonucleotide (lanes 6 and 7), resides in the 60 kd polypeptide, RIP60.

Hence an oligonucleotide column fraction that exhibited maximal specific DNA binding was incubated with uniformly radiolabeled ATT oligonucleotide probe in the presence or absence of specific competitor DNA. After UV irradiation and processing of the samples (see Experimental Methods), autoradiography of the SDS gel revealed several labeled bands in the absence of any competitor (FIG. 4, lane 1). Labeling of a 60 kD protein was reproducibly prevented by either the ATT or ORI oligonucleotide competitors (FIG. 4, lanes 2-5). In contrast, a nonspecific control competitor, the H4 oligonucleotide, had no effect of the 60 kD polypeptide (FIG. 4, lanes 6-7). These results establish that the 60 kD protein which coelutes with the specific DNA binding activity is indeed the ATT-binding factor. This 60 kD origin binding protein is referred to as RIP60.

EXAMPLE 3

DNA Bending is Not Sufficient for Binding of RIP60

Figure 5:
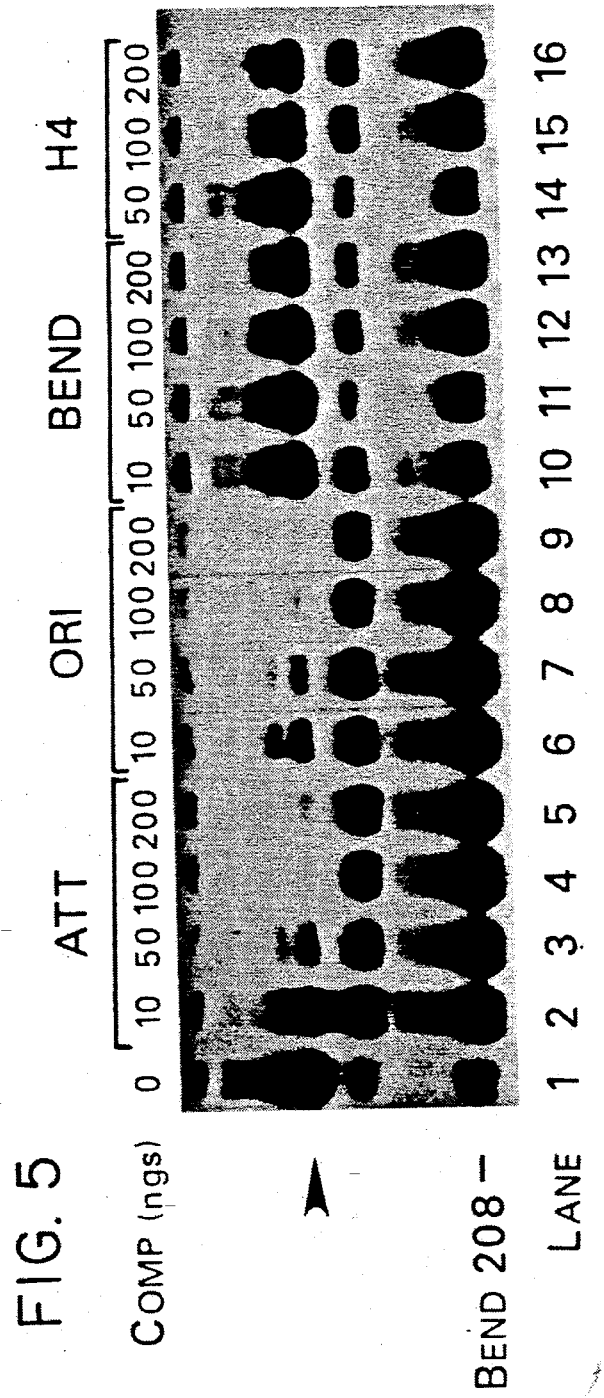
FIG. 5 demonstrates that DNA bending alone is insufficient for RIP60 binding. An end-labeled probe encompassing the dhfr bent DNA sequences (bend 208) was incubated with a fraction from the first DNA affinity column that exhibited maximal specific DNA binding activity, and protein-DNA complexes were resolved by electrophoresis on a 4% neutral polyacrylamide gel. Autoradiography shows that oligonucleotide competitors containing either repeated ATT motifs (ATT, lanes 2-5) or sequences from the dhfr origin region that encompass the RIP60 binding site (ORI, lanes 6-9) inhibit the formation of specific RIP60 protein/bend 208 DNA complexes (arrow). In contrast, neither bent DNA alone (BEND, lanes 10-13) nor sequences from the human histone H4 promoter region (H4, lanes 14-16) are able to inhibit the formation of RIP60/bend 208 complexes.

DNA binding proteins may recognize bent DNA as a structural feature of the DNA rather than as a specific nucleotide sequence per se. To determine if DNA bending alone was sufficient for RIP60 to bind DNA, the ability of various oligonucleotides to compete for RIP60 binding to the dhfr origin sequences or the ATT oligonucleotide in gel shift assays was analyzed. As shown in FIG. 5, either the ATT oligonucleotide (ATT, lanes 2-5) or the dhfr origin oligonucleotide which includes bend elements B2-B5 and the ATT repeats (ORI, lanes 6-9), compete effectively for binding of the purified factor to a 208 bp probe encompassing the bent dhfr origin sequences. By contrast, a double stranded oligonucleotide that spans bend elements B1-B4 but lacks the ATT repeats (designated BEND) is an ineffective competitor of RIP60 binding, even at high concentrations (FIG. 5, lanes 10-13).

Because the ability of the BEND oligonucleotide to induce stable DNA bending in new sequence contexts has been independently confirmed by cyclic permutation assays (M. Caddle and N. H. Heintz, unpublished observations), it has been concluded that binding of RIP60 to DNA is directly solely by the tandem ATT repeats, and does not require bend DNA. Identical competition profiles are obtained when the ATT oligonucleotide rather than the dhfr origin sequence is used as probe (data not shown).

EXAMPLE 4

RIP60 Binds to Domain B of the Yeast Origin of Replication, ARS1

Reasoning that factors involved in regulating DNA replication may be conserved between species, it was sought to determine if RIP60 would recognize another, well defined eukaryotic origin of replication. ARS1, an autonomously replicating sequence element of the yeast *Sacchromyces cerevesiae* that has been shown to function as an origin of replication in vivo (reviewed in Umek, R. M. et al., (1989). BIOCHIMICA ET BIOPHYSICA ACTA, 1007, 1-14), was selected for these experiments. Deletion and point mutagenesis of ARS1 reveal at least three functional domains; domain A contains the 11 bp consensus sequence required for ARS activity (Kearsey, S. (1984). CELL, 37:299-307; Celniker, S. E. et al., (1984). MOL. CELL. BIOL., 4, 2455-2466), domain B contains an AT-rich region that includes bent DNA and is required for efficient ARS activity under certain growth conditions (Snyder, M. et al., (1986), NATURE, 324, 87-89; Williams, J. S. et al., (1988). MOL. CELL. BIOL., 8, 2763-2769), and domain C contains sequences whose function is incompletely characterized (Celniker, S. E. et al., (1984). MOL. CELL. BIOL., 4, 2455-2466).

Figure 6A:
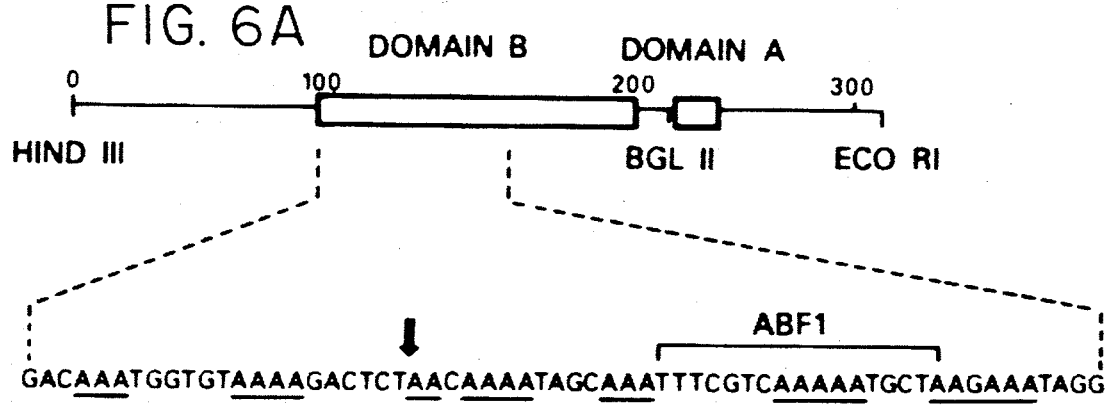
FIG. 6 demonstrates that RIP60 binds to domain B of the yeast origin of replication, ARS1. 6A) Schematic representation of the 311 EcoR1-HindIII fragment of ARS1. Domain A of ARS1 encompasses the 11 bp consensus sequence required for ars activity (small open box). Domain B (large open box) encompasses a 41 bp region that enhances 2ARS1 activity under certain growth conditions (Synder et al., 1986): indicated by solid lines are the oligo dA tracts that contribute to sequence-directed DNA bending in domain B. The binding site for the yeast factor ABF1 is also indicated. The vertical arrow indicates the position of a strong DNAse Hypersensitive site observed in footprinting experiments with RIP60 and the HindIII-BglII domain B fragment. 6B, 6C, 6D) Analysis of RIP60/ARS1 interactions by the gel electrophoresis mobility shift assay. Partially purified RIP60 was incubated with the indicated end-labeled probes in the presence of various concentrations of the designated oligonucleotide competitors. Protein-DNA complexes were resolved by neutral PAGE and visualized by autoradiography. Specific RIP60 protein/ARS1 DNA complexes detected in each experiment are indicated by arrows. Panel 6B: RIP60 binding to the full length 311 bp EcoR1-HindIII probe of ARS1. Panel 6C: RIP60 binding to the HindIII-BglII domain A probe. Panel 6E. Competition analysis of RIP60 binding. An end-labeled ORI DNA probe was incubated with partially purified RIP60 and various concentrations of the indicated competitor DNA. Specific RIP60/ORI DNA complexes (arrow) were visualized by the gel shift assay. Note that while the domain B restriction fragment competes for RIP60 binding with about 10-fold lower affinity than the ATT oligonucleotide (compare lanes 2 and 3), neither the ABF1-specific E1 oligonucleotide (lanes 5-7) nor the GRFI-specific E2 oligonucleotide lanes (8-10) compete for RIP60 binding.
Figure 6B:
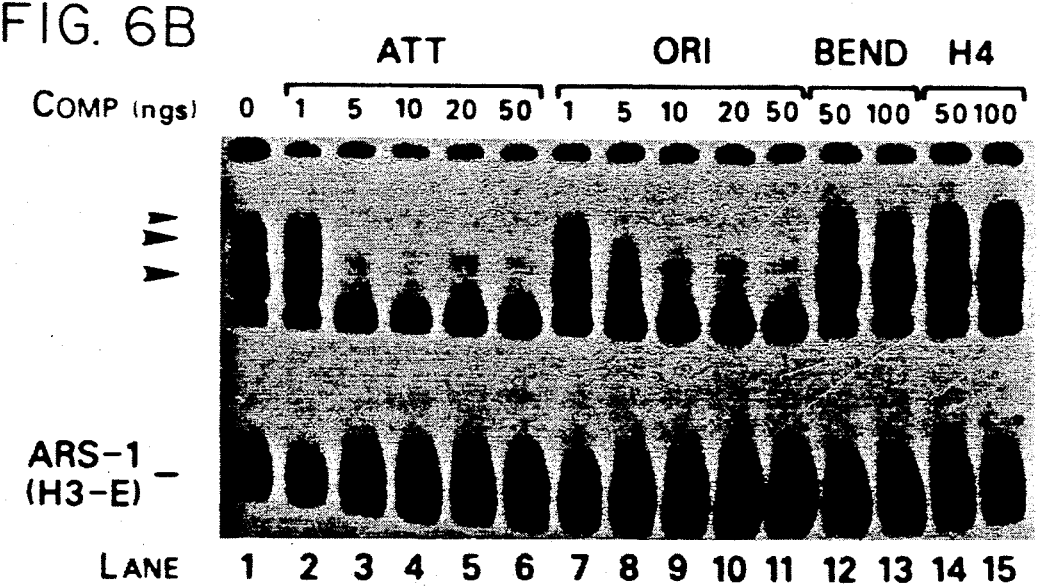
Figure 6C:
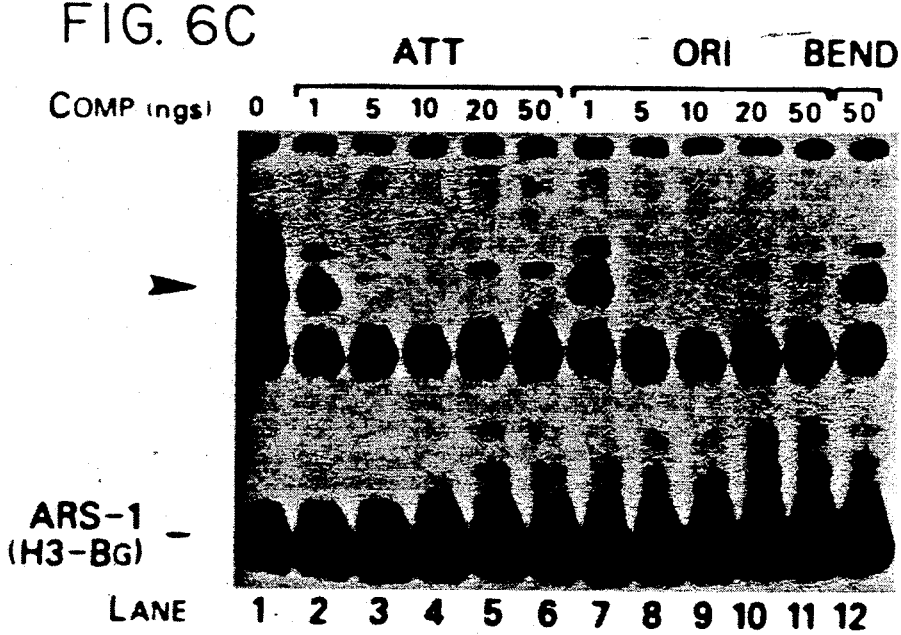
Figure 6D:
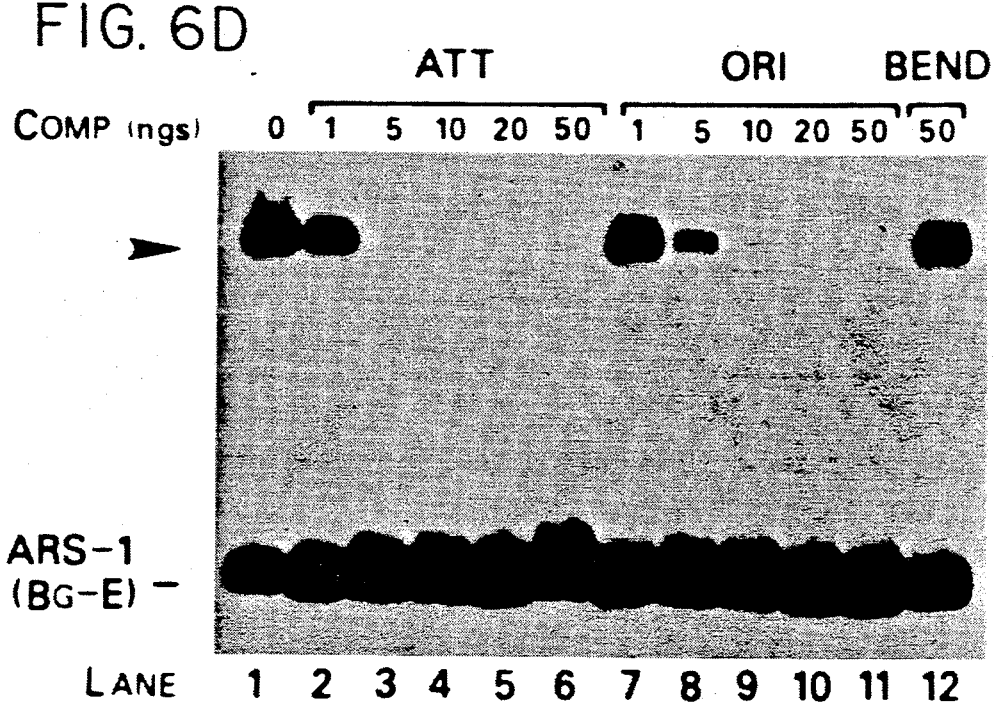

To determine if RIP60 binds to ARS1, gel shift and DNAse I footprinting experiments were performed with a 311 bp Hind III-Eco R1 fragment of ARS1 that includes both domains A and B (see FIG. 6A). This probe was incubated with either the S sepharose 0.5M KCl step fraction or oligonucleotide column-purified RIP60 in binding competition experiments. As shown in FIG. 6B, RIP60 exhibits specific binding to ARS1, albeit with about a 10-fold lower affinity as compared to either the ATT or ORI DNA probes (see lanes 2-12, FIG. 6B). Note that the competition assays suggest that the HeLa factor forms multiple specific complexes with the 311 bp ARS-1 probe (arrows, FIG. 6B).

To map the position of factor binding to ARS1 more precisely, probes containing either domain A or domain B were generated by digestion with Bgl II and Eco R1, or Bgl II and Hind III, respectively. As shown in FIG. 6, RIP60 formed protein-DNA complexes with both the domain A (panel 6D) and domain B probes (panel 6C), and these complexes were competed with the same specificity as those observed for the 311 bp fragment. To better delineate the binding site within domain B, a series of DNAse I footprinting experiments were performed using a wide range of conditions. Although binding of RIP60 induces a strong, specific DNAse I hypersensitive site that maps within the 41 bp bent DNA region of domain B that is known to enhance ARS1 function (see FIG. 6A), a clear protected region in these experiments could not be observed (data not shown). In spite of the inability to observe a discrete footprint in domain B, the gel shift results clearly demonstrate the RIP60 binds specifically to a sequence within domain B of ARS1.

Figure 6E:
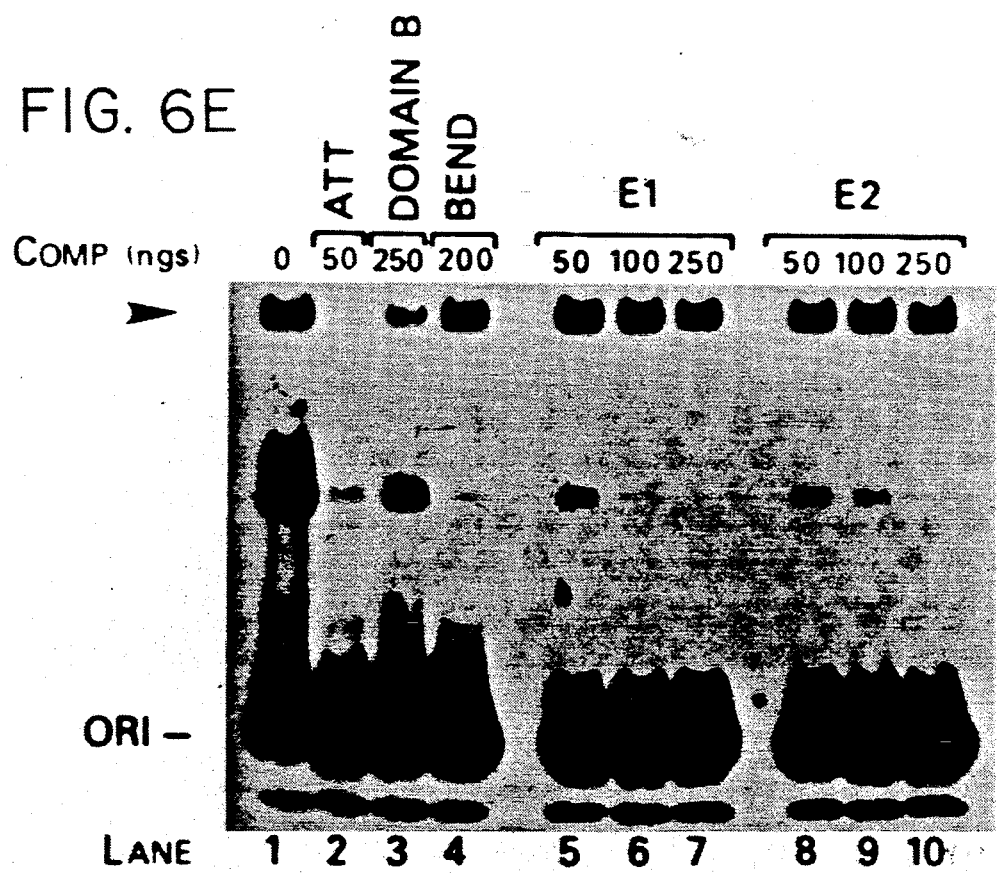

It has been shown that the 3' end of domain B contains a binding site for ABF1, a yeast factor that binds upstream of several promoters as well as to several ars elements, silencers, and telomeres (Buchman et al, 1988, and references therein). To determine if RIP60 represents a mammalian homolog of ABF1, binding experiments were performed using the diagnostic oligonucleotides E1, which contains a consensus wild type ABF1 binding site, or E2, which contains a consensus binding site for a second yeast ars binding factor, GRF1 (Buchman, A. R. et al. (1988). MOL. CELL. BIOL. 8, 210-225, as competitors. As shown in FIG. 6E, neither E1 (lanes 5-7) nor E2 (lanes 8-10) are able to compete for binding of RIP60 to the dhfr origin probe, while the domain B fragment of ARS1 competes for binding with an approximately 10-fold lower affinity than the ATT oligonucleotide (compare lanes 2 and 3, FIG. 6E). These results demonstrate that RIP60 specifically binds to domain B of ARS1 at a site which is distinct from that of ABF1, and that RIP60 is not directly analogous to either ABF1 or GRF1. Although the gel shift experiment depicted in FIG. 6D indicates that RIP60 also recognizes a sequence(s) outside of domain B, this interaction has not yet been characterized.

EXAMPLE 5

The Origin Binding Activity of RIP60 Copurifies with a DNA Helicase

As described earlier herein, an essential event in the initiation cascade is the localized unwinding of origin DNA by DNA helicases. To determine if the highly purified fractions containing RIP60 also contained helicase activity, a standard oligonucleotide displacement assay was employed (Lahue, E. E., & Matson, S. W. (1988). J. BIOL. CHEM., 263, 3208-3215). The substrate for these experiments was a partially double stranded DNA molecule composed of an end-labeled 18 base oligonucleotide annealed to circular single stranded M13 DNA. Unwinding of the double stranded portion of the substrate by a helicase causes release of the oligonucleotide, which can be monitored by electrophoresis of the reaction on nondenaturing polyacrylamide gels and autoradiography. Thus, helicase activity was assessed by incubating the labeled substrate with RIP60-containing fraction from the second oligo affinity column in the presence or absence of different nucleotides; control reactions were incubated without protein in the presence of ATP.

Figure 7:
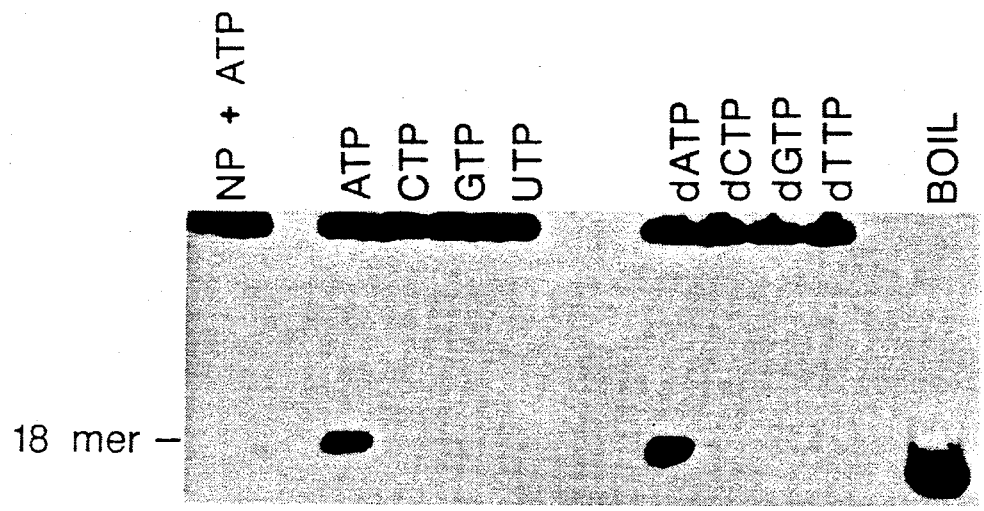
FIG. 7 demonstrates that purified RIP60 contains an ATP or dATP-dependent DNA helicase activity. A partially double-stranded DNA duplex consisting of an end labeled 18 mer annealed to single-stranded M13mp18DNA was incubated with a RIP60 fraction from the second DNA affinity column in the presence of the indicated nucleotide triphosphate (see Experimental Procedures for details). Displacement of the labeled 18 mer was monitored by neutral PAGE and autoradiography. Control reactions were incubated with ATP and without protein (NP+ATP). Boiling of the substrate in the presence of protein and ATP for 10 min releases intact 18 mer (Boil).

After incubation at 37° C., displacement of the oligonucleotide was monitored by neutral PAGE and autoradiography as described above. As depicted in FIG. 7, helicase activity was observed in the presence of RIP60 when ATP or dATP was included in the reaction. In contrast, no displacement of the labeled oligonucleotide was observed in the absence of protein, or in the presence of CTP, GTP or UTP, or their deoxyribonucleotide analogs. These results indicate that both an origin-specific DNA binding activity and an ATP (or dATP)-dependent DNA helicase activity are present in the most highly purified preparations of RIP60 from the ATT-oligonucleotide affinity column.

EXAMPLE 6

Covalent Radiolabeling of the DNA Helicase with ATP

Although the final preparation of RIP60 had been purified more than 8,500-fold, other polypeptides in addition to RIP60 were visible on silver stained SDS gels (see FIG. 3). It was sought to determine if the DNA helicase activity was inherent to RIP60, or could be attributed to another protein. Since the results of the oligonucleotide displacement assays indicated that the helicase requires ATP (or dATP) for activity, it was reasoned that covalent labeling of the protein preparation with [alpha-$^{32}$P]ATP would identify the protein species with helicase activity. This assay was successfully employed by Sopta et al. (1989) to identify the helicase of the RAP30/74 transcription complex as RAP74.

Hence, a RIP60-containing fraction from the final oligonucleotide affinity column was incubated in the presence of [alpha-$^{32}$P]ATP, the reaction was terminated by boiling in SDS, and the samples were then resolved by SDS-PAGE. The location of protein molecular weight markers was determined by silver staining; labeled proteins were identified by autoradiography.

Figure 8:
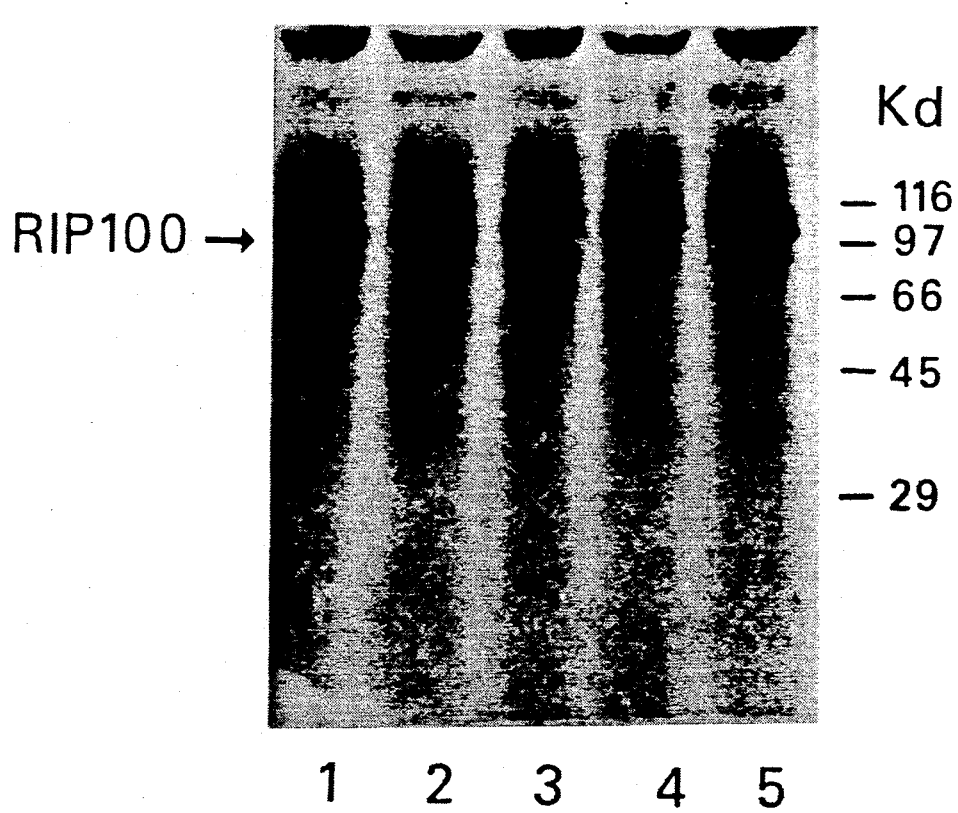
FIG. 8 demonstrates that covalent radiolabeling with ATP identified a 100 kd polypeptide as the DNA helicase. A RIP60 fraction from the second oligonucleotide affinity column was incubated with [alpha-$^{32}$P]ATP in the absence (lane 1) or presence of 0.1 mM unlabeled ATP (lane 2), CTP (lane 3), GTP (lane 4), or UTP (lane 5). After 1 min on ice and 1 min at room temperature, samples were boiled in SDS and resolved by SDS-PAGE. Protein molecular weight markers were visualized by silver staining (not shown); labeled polypeptides were visualized by autoradiography. The 100 kd polypeptide labeled under these conditions is designated RIP100.

As FIG. 8 clearly shows, incubation of the most highly purified RIP60 fraction with [alpha-$^{32}$P]ATP resulted in covalent labeling of a single polypeptide of 100 kD, and not RIP60. Competition with different ribonucleotides revealed that the 100 kD protein, named herein RIP100, bound NTPs in a manner that was consistent with the activity of the helicase; only excess cold ATP but not CTP, GTP, or UTP were effective competitors for labeling of RIP100 with [alpha-$^{32}$P]ATP (FIG. 8, lanes 2-5). Moreover, incubation of the RIP60 protein preparation with [alpha-$^{32}$P]GTP did not label RIP100 (data not shown).

To delineate the relationship between the DNA binding, the DNA helicase, and the ATP-labeling activities, 60 fractions eluted from the second oligonucleotide column by a continuous salt gradient from 0.2 to 1.0M KCl were first assayed for RIP60 specific-DNA binding activity. Selected fractions from the portion of the gradient that encompassed the peak of DNA binding activity were then compared for each of three activities; DNA binding, DNA helicase, and covalent radiolabeling with ATP. Shown in FIG. 9 are protein constituents of the relevant fractions as visualized by silver staining (9A), and the elution profiles for the DNA binding activity (9B), the DNA helicase activity (9C), and the ATP-labeling activity (9D).

Quantitation of the DNA binding shows that RIP60 binding activity peaks at fractions 32-33, while the DNA helicase activity peaks slightly earlier in fractions 30-32. The 100 kD protein, RIP100, is clearly visible in these fractions. Vigorous radiolabeling of RIP100 is evident in fraction 30, and continues to be observed throughout fractions 32-34. Taken together, these results shown that the DNA helicase is likely identical to the ATP binding protein, RIP100, and that these activities closely coelute with the origin-specific DNA binding activity of RIP60.

DISCUSSION

The evidence obtained by extensive origin mapping studies indicates that a chromosomal origin of DNA replication is located within a short region 3' to the Chinese hamster dhfr gene. Although precise definition of the sequences required for dhfr origin activity has been thwarted by the lack of suitable genetic or biochemical assays, recent high resolution mapping experiments using two independent methods have located initiation events at the dhfr origin to within 800 bp of the bent DNA sequences described in FIG. 1 (W. C. Burhams, M. S. Caddle, N. H. Heintz, and M. DePamphilis, in preparation). This portion of the dhfr origin region encompasses several elements characteristic of origins of replication, including stably bent DNA and binding sites for two well characterized transcription factors associated with cell proliferation, AP1 (Angel et al., 1987) and OTF1/NFIII (O'Neill et al., 1988). These features prompted the search for other nuclear proteins which display the activities expected of factors involved in initiation of DNA replication. Accordingly, this study has resulted in the characterization of a highly purified protein preparation that exhibits both origin-specific DNA binding and DNA helicase activities; these proteins have been designated RIP60 and RIP100 respectively.

The properties of RIP60 and RIP100 distinguish these factors from two other cellular factors which are known to participate in viral DNA replication in vitro; competition experiments, apparent molecular weight and chromatographic behavior distinguish RIP60 and RIP100 from both NF1 (Rosenfeld, P. J., & Kelly, T. J. (1986). J. BIOL. CHEM. 261, 1398–1408) and OTF1/NFIII (O'Neill, E. A. et al. (1988), and references therein). The binding properties of RIP60 also distinguish this factor from alpha-binding protein, a ubiquitous nuclear factor that binds to sequences comprised of any combination of six A+T base pairs (Solomon, M. J. et al. (1986). PROC. NATL. ACAD. SCI. USA, 83, 1276–1280).

In addition, competition experiments indicate that RIP60 is not a mammalian homolog of the yeast protein, ABF1 (Buchman et al., 1988). Although the nucleotide requirements for the DNA helicase activity of RIP100 are identical to those of the general transcription initiation factor complex RAP30/74, RIP100 is unlikely to be a portion of RAP30/74 since the transcription factor complex is comprised of three polypeptide components of 74, 38 and 30 kD (Sopta et al., 1989), none of which correspond to the molecular weight of RIP100. Moreover, the covalent radiolabeling experiments with ATP identify a 100 kD protein as the DNA helicase, whereas the same experiment with RAP30/74 labels a 74 kD polypeptide (Sopta et al., 1989). Thus, it is believed that RIP60 and RIP100 represent novel activities.

A Role for RIP60 and RIP100 in DNA Replication

While it is not possible at this time to directly assess the role of RIP60 and RIP100 in the initiation of chromosomal DNA replication, it is believed that several of the above experimental results strongly support this possibility. First, the RIP60 binding site is located immediately 3' to the bent DNA sequences within a 20 bp AT-rich sequence. The position of the RIP60 binding site relative to the bent DNA motif is strikingly reminiscent of the juxtaposition of AT-rich or bent DNA elements and initiation protein binding sites in a number of well characterized origins of replication. As discussed earlier, the bent DNA sequences and its attendant RIP60 binding site are located adjacent to the immediate initiation zone of the dhfr origin region. Secondly, RIP60 is able to bind specifically to DNA sequences within the functionally important domain B of the yeast origin, ARS1. Since the protein factors that mediate replication from ARS1, or other yeast origins, have not been identified, it is possible that an analog of RIP60-/RIP100 participates in initiation of DNA synthesis in yeast.

The copurification of RIP60 and RIP100 further support the contention that these proteins are initiation factors. The purification protocol developed and used results in a greater than 8,500-fold purification of the dhfr origin-specific DNA binding activity, and UV crosslinking experiments establish that this binding activity resides in the 60 kD polypeptide, RIP60. The ATP labeling experiments indicate that a 100 kD polypeptide present in the final protein preparation covalently binds ADP during the hydrolysis of ATP, and strongly suggests the DNA helicase activity that copurifies with the origin binding activity resides in the 100 kD protein, RIP100. This interpretation also is supported by competition experiments in which it is observed that ATP, but no other ribonucleotide, is able to inhibit radiolabeling of the 100 kD protein. It is therefore believed that the copurification of the origin-specific DNA binding protein, RIP60, with the ATP-dependent helicase, RIP100, after five chromatographic steps is compelling evidence that these factors participate in initiation of chromosomal DNA synthesis.

The experimental results presented here suggest that the RIP60 and RIP100 polypeptides may act together to unwind the DNA template during initiation of DNA synthesis. There is ample precedent for such a mechanism. In E. coli, the origin recognition factor, dnaA, binds to DNA sequences at the chromosomal origin of replication, oriC, and potentiates the opening of a local AT-rich repeated region (Bramhill and Kornberg, 1988). This protein-DNA complex then serves as a substrate for duplex unwinding by dnaB, the helicase required for initiation of DNA replication (Baker et al., 1987). A similar series of ordered interactions between an origin recognition protein and the dnaB helicase also mediates initiation of lambda phage DNA replication (Schnos et al., 1988, and references therein). Interestingly, functional interaction of lambda origin binding factors is promoted by DNA bending (Zahn, K., & Blattner, F. (1987). NATURE, 317, 451–453). By analogy, it is possible that the DNA binding activity of RIP60 directs the DNA helicase activity of RIP100 to a higher order structure at the dhfr origin, and both factors then cooperate to unwind the origin during initiation of DNA synthesis. Although eukaryotic viruses may utilize a single protein (e.g. SV40 large T-antigen) for both origin recognition and origin unwinding, there is no evidence for such a factor in mammalian cells.

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

What is claimed is:

1. A method for measuring the binding sites for a protein material selected from the group consisting of a replication initiator protein complex for eukaryotic cells, said protein complex comprising a 60 kD fraction and a 100 kD fraction; a 60 kD protein fraction of said protein complex; and a 100 kD fraction of said protein complex; said protein material comprising in all cases a protein in purified form, and in the case of said protein complex capable of origin-specific DNA binding and ATP-dependent DNA helicase activity, in the case of said 60 kD protein fraction primarily capable of origin-specific DNA binding, and in the case of said 100 kD protein fraction primarily capable of ATP-dependent DNA helicase activity, wherein the binding sites for said protein material are measured by:

A. providing at least one sample of said protein material;

B. placing a detectible label on said protein material sample;

C. placing a labeled protein material sample in contact with a biological sample from a mammal in which binding sites for said protein material are suspected; and D. detecting the presence of labeled protein material bound to said biological sample as an indication of the presence of binding sites.

2. A method of testing the ability of a drug or other agent to modulate the activity of a protein material which comprises:

A. culturing a colony of test cells which has a receptor for the protein material in a growth medium containing the protein material;

B. adding the drug or agent under test;

C. measuring the binding of said protein material with the receptor on said test cells, said protein material selected from the group consisting of a replication initiator protein complex for eukaryotic cells, said protein complex comprising a 60 kD fraction and a 100 kD fraction; a 60 kD protein fraction of said protein complex; and a 100 kD fraction of said protein complex; said protein material comprising in all cases a protein in purified form, and in the case of said protein complex capable of origin-specific DNA binding and ATP-dependent DNA helicase activity, in the case of said 60 kD protein fraction primarily capable of origin-specific DNA binding, and in the case of said 100 kD protein fraction primarily capable of ATP-dependent DNA helicase activity;

D. comparing the binding measured in Step C with the binding measured on test cells under the same conditions in the absence of drug or agent under test as an indication of the ability of said drug or agent to modulate the activity of said protein material.

3. A method of screening drugs and other agents for ability to modulate the production of a protein material which comprises:

A. inocculating an observable cellular test colony with a drug or agent;

B. disrupting the cells and obtaining the resultant supernatant therefrom;

C. examining said supernatant for the presence and determining the amount of said protein material, said protein material selected from the group consisting of a replication initiator protein complex for eukaryotic cells, said protein complex comprising of 60 kD fraction and a 100 kD fraction; a 60 kD protien fraction of said protein complex; and a 100 kD protein fraction of said protein complex; said protein material comprising in all cases a protein in purified form, and in the case of said protein complex capable of origin-specific DNA binding and ATP-dependent DNA helicase activity, in the case of said 60 kD protein fraction primarily capable of origin-specific DNA binding, and in the case of said 100 kD protein fraction primarily capable of ATP-dependent DNA helicase activity;

D. comparing the amount of protein material measured in Step C with the protein material produced by a test colony under the same conditions in the absence of drug or other agent under test as an indication of the ability of said drug or agent to modulate the production of said protein material.

* * * * *